United States Patent [19]
Salmond et al.

[11] Patent Number: 5,871,922
[45] Date of Patent: Feb. 16, 1999

[54] GENES INVOLVED IN THE BIOSYNTHETIC PATHWAY OF CARBAPENEM

[76] Inventors: George Peacock Copeland Salmond, 4 Lancaster House, 36 Clarendon Square, Leamington spa Warwickshire, United Kingdom, CU32 5Q7; Simon James McGowan, 28 Fir Grove, Tile Hill, Coventry, United Kingdom, CU4 9FU; Mohammed Sebaihia, 58 Arnold Avenue, Styvechale, Coventry, United Kingdom, CU3 5LX; Anthony Richard John Cox, 2 Priest Park View, Chadwick End, Solihull, United Kingdom, B93 0BP; Matthew Thomas Geoffrey Holden, CHZ/110, Cryfield Halls, University of Warwick, Coventry, United Kingdom, CU4 7AL; Lauren Elizabeth Porter, 46 Beacon Way, Rickmansworth, Hortfordshire, United Kingdom, WD3 2PE; Barrie Walsham Bycroft, 14 The Closters, Nottingham, United Kingdom, NG9 2FR; Paul Williams, 67 Gunnersbury Way, Nottingham, United Kingdom, NG16 1QO; Gordon Sidney Anderson Birnie Stewart, 14 James Avenue, Loughborough, United Kingdom, LE11 5QL

[21] Appl. No.: 737,825

[22] PCT Filed: May 18, 1995

[86] PCT No.: PCT/GB95/01125

§ 371 Date: Jun. 3, 1997

§ 102(e) Date: Jun. 3, 1997

[87] PCT Pub. No.: WO95/32294

PCT Pub. Date: Nov. 30, 1995

[30] Foreign Application Priority Data

May 20, 1994 [GB] United Kingdom ................ 9410142.5

[51] Int. Cl.$^6$ ........................... C12Q 1/68; C07H 21/04; C12P 19/34; C07K 14/00
[52] U.S. Cl. ........................ 435/6; 435/91.2; 435/320.1; 536/23.7; 530/350; 935/77; 935/78
[58] Field of Search .............................. 435/91.2, 320.1, 435/6, 69.1; 536/23.7, 24.32; 530/350; 935/77, 78

[56] References Cited

FOREIGN PATENT DOCUMENTS 1-1043191  2/1989  Japan .

OTHER PUBLICATIONS

Hase et al. Biochim. Biophys. ACTA 744(1):46–52, 1983.
Swift et al. Molecular Microbiology 10(3):511–520, 1993.
McGowan et al. Molecular Microbiology 22(3):415–426, 1996.
Keller et al. DNA Probes. M Stockton Press, New York, N.Y., pp. 255–259, 325–337, 1993.

Primary Examiner—Lisa B. Arthur
Attorney, Agent, or Firm—Birch, Stewart Kolasch & Birch LLP

[57] ABSTRACT

DNA involved in the bacterial gene expression of carbapenem antibiotics comprising: a) at least one of the genes carA, carB, carC, carD, carE, carF, carG, carH, b) DNA capable of hybridizing to any of the genes defined in a) and capable of functioning as such genes in the biosynthetic pathway of a carbapenem, c) DNA which is a) or b) above by virtue of the degeneracy of the genetic code. Polypeptides encoded by such DNA.

17 Claims, 17 Drawing Sheets

Figure 4A

```
         10         20         30         40         50
AGATCGGCGCACTGCGTGCCTTTGGCGACGCCGCGTTACGGCATTTTCAC 60         70         80         90        100
GCTGATTTGGAGCGGGCTGATGTCGCTGGTGAGCGTCGGCGTGCTGCTGG 110        120        130        140        150
GTGTCGGTCTGGGCTACCTTGCCGCCCGCGCGATTGCGGTGGTGATGAGT 160        170        180        190        200
GAGAAAGCGGTTTTGTCCTGCCGGTGACGTTGGAATGGGAAGACATCCA 210        220        230        240        250
CTTCGTCCTGCTCCTGTTGCTGGTCGCCGCTGTTGTCCTGACGATTCCGG 260        270        280        290        300
CGATGCTGTCCTACCGTCAATCTCCTGCTACGGCGCTGCGTGGCGAGTAA 310        320        330        340        350
TAGGGTTGCGACTCAGTCGCAAAACTAAGCTGTAGTGGCATCGGACGTGT 360        370        380        390        400
AGTTCTCTGCGTCCGATGCTGTTTTTCCTTACCTATTCATCCCTTCCGA 410        420        430        440        450
TTCTCATACTCACTCAACGGCCTTCGTCCTTCGGTATTATGGTTTGGGGC 460        470        480        490        500
CAGTAACGAGCAGTAATACTGTTACTTATTTCGCTAAATAATATTTATAA 510        520        530        540        550
TAATAGTAACTCTATCAATTATTATTGAATTATTAGTATATAAAATGTTG 560        570        580        590        600
ACTGATTGTATATTAATTGATAACTTTCGACCTTGTTAAATCCTAGTGAT 610        620        630        640        650
TATATTTGGTGTAACTAAAAATAATTATATTTACTCTCTGGTAAAGAGTT 660        670        680        690        700
GATCTTTTAATCTTTGAGCAAAGTCGGTAAGAGAGGGTAATATGGATCAT
                                       CarR  M  D  H 710        720        730        740        750
GAAATCCATTCCTTTATCAAAAGGAAGTTGAAAGGAGTCGGTGATGTATG
 E   I   H  S   F   I   K   R   K   L   K  G  V  G  C  V  W
```

Figure 4B

```
       760        770        780        790        800
GTTTTCTTATTTTATGATGAGTAAAAACTCTACCAGCCAACCTTATATTA
  F  S  Y  F  M  M  S  K  N  S  T  S  Q  P  Y  I 810        820        830        840        850
TTTCGAATTATCCAGAAGCATGGATGAAGGAGTATATAAAAAAGAGATG
  I  S  N  Y  P  E  A  W  M  K  E  Y  I  K  K  E  M 860        870        880        890        900
TTTCTGAGTGATCCTATCATTGTTGCCTCATTAGCTCGGATCACGCCGTT
  F  L  S  D  P  I  I  V  A  S  L  A  R  I  T  P  F 910        920        930        940        950
TTCTTGGGATGATAATGATATTGTGACGCTAAGAGCCAAGAATCAGGATG
  S  W  D  D  N  D  I  V  T  L  R  A  K  N  Q  D 960        970        980        990       1000
TCTTTATTTCTTCCGTGCAGCACGATATAAGTTCAGGTTATACCTTTGTT
  V  F  I  S  S  V  Q  H  D  I  S  S  G  Y  T  F  V 1010       1020       1030       1040       1050
TTGCACGACCATGATAATAATGTGGCGACACTGAGTATAGCGAATCACTT
  L  H  D  H  D  N  N  V  A  T  L  S  I  A  N  H  L 1060       1070       1080       1090       1100
GGAAGATGCGAATTTCGAAAAATGTATGAAGAATCATGAAAATGATTTGC
  E  D  A  N  F  E  K  C  M  K  N  H  E  N  D  L 1110       1120       1130       1140       1150
AGATGTTACTTGTGAATGTACATGAAAAAGTGATGGCCTATCAGCGAGCT
  Q  M  L  L  V  N  V  H  E  K  V  M  A  Y  Q  R  A 1160       1170       1180       1190       1200
ATCAACGATCAAGATAACCCCCCCGATAATTCAAGAAACGCCTTACTCTC
  I  N  D  Q  D  N  P  P  D  N  S  R  N  A  L  L  S 1210       1220       1230       1240       1250
TCCGCGTGAAACCGAAGTTCTTTTCCTGGTTAGTAGTGGACGAACTTACA
  P  R  E  T  E  V  L  F  L  V  S  S  G  R  T  Y 1260       1270       1280       1290       1300
AAGAGGTTTCCCGTATATTAGGTATTAGTGAGGTCACCGTTAAGTTCCAC
  K  E  V  S  R  I  L  G  I  S  E  V  T  V  K  F  H
```

Figure 4C

```
       1310        1320        1330        1340        1350
ATTAACAACTCAGTCCGTAAATTGGATGTTATCAATTCCCGCCATGCTAT
  I  N  N  S  V  R  K  L  D  V  I  N  S  R  H  A  I 1360        1370        1380        1390        1400
AACTAAAGCACTTGAGTTAAATCTTTTCCATTCCCCCTGTGAACCTGTAG
   T  K  A  L  E  L  N  L  F  H  S  P  C  E  P  V 1410        1420        1430        1440        1450
TGATGAAGCATATGGACGCCCGTTAGCGTGTATTAATGCTTGATAATAGG
 V  M  K  H  M  D  A  R  *

1460        1470        1480        1490        1500
GAGGTACCTATCCAAAAGAATAGTAACTCCCTATCTAAAAGAAATACATT
           Sspi                                 EcoR1

1510        1520        1530        1540        1550
AGCTGAACTTTTACACGGTTAATATTTACCCTCGCCTTTTCTATGATATG
                                                  carA 1560        1570        1580        1590        1600
TGACGAATTCAAACGTTGTTTTCTCTCATGTTGTTATTAAGGTAAGGGTT
 V  T  N  S  N  V  V  F  S  H  V  V  I  K  V  R  V 1610        1620        1630        1640        1650
ATTACTGTGAGCAATAGTTTTTGCGTTGTTTATAAAGGTTCTGATACCGA
  I  T  V  S  N  S  F  C  V  V  T  K  G  S  D  T  D 1660        1670        1680        1690        1700
TATAAATAATATCCAACGCGACTTCGACGGAAAGGGCGAACGATTATCTA
   I  N  N  I  Q  R  D  F  D  G  K  G  E  R  L  S 1710        1720        1730        1740        1750
ATGGCTATCTTTTTATCGAACAGAATGGCCATTATCAGAAGTGTGAGATG
 N  G  Y  L  F  I  E  Q  N  G  H  Y  Q  K  C  E  M 1760        1770        1780        1790        1800
GAAAGAGGAACGGCCTACCTGATAGGCTCGCTGTACAATCGGACGTTTCT
  E  R  G  T  A  Y  L  I  G  S  L  Y  N  R  T  F  L 1810        1820        1830        1840        1850
GATCGGATTGGCCGGTGTGTGGGAAGGCGAGGCTTATCTGGCAAATGATG
   I  G  L  A  G  V  W  E  G  E  A  Y  L  A  N  D
```

Figure 4D

```
      1860        1870        1880        1890        1900
CCGAGCTGTTAGCGTTGCTGTTCACGCGTTTGGGAGCGAATGCACTGGCG
 A   E   L   L   A   L   L   F   T   R   L   G   A   N   A   L   A 1910        1920        1930        1940        1950
CTGGCTGAAGGTGCATTCTGCTTTTCTTATGAGCCAAACGGCGAATTGAC
 L   A   E   G   A   F   C   F   S   Y   E   P   N   G   E   L   T 1960        1970        1980        1990        2000
GGTGATTACCGAGTCGCGTGGTTTCTCGCCGGTTCATGTCGTACAGGGCA
   V   I   T   E   S   R   G   F   S   P   V   H   V   V   Q   G 2010        2020        2030        2040        2050
AAAAAGCCTGGATGACCAATAGCCTTAAACTGGTTACTGCGGCAGAAGGT
 K   K   A   W   M   T   N   S   L   K   L   V   T   A   A   E   G 2060        2070        2080        2090        2100
GAAGGCGCGCTGTGGTTTGAAGAAGAGGCGTTGGTGTGCCAGTCGCTGAT
   E   G   A   L   W   F   E   E   E   A   L   V   C   Q   S   L   M 2110        2120        2130        2140        2150
GCGAGCGGATACCTATACGCCGGTGAAAAATGCGCAGCGTCTTAAGCCGG
   R   A   D   T   Y   T   P   V   K   N   A   Q   R   L   K   P 2160        2170        2180        2190        2200
GAGCGGTGCATGTTCTTACGCACGATAGCGAAGGTTATTCTTTCGTTGAA
 G   A   V   H   V   L   T   H   D   S   E   G   Y   S   F   V   E 2210        2220        2230        2240        2250
AGCCGCACGCTGACCACACCAGCCAGCAACCAATTGTTAGCGCTCCCGCG
   S   R   T   L   T   T   P   A   S   N   Q   L   L   A   L   P   R 2260        2270        2280        2290        2300
TGAACCGCTGCTGGCATTGATTGATCGCTACCTTAATGCTCCGCTTGAGG
   E   P   L   L   A   L   I   D   R   Y   L   N   A   P   L   E 2310        2320        2330        2340        2350
ATTTAGCGCCGCGCTTTGATACCGTAGGAATTCCCTTGTCAGGCGGTCTG
 D   L   A   P   R   F   D   T   V   G   I   P   L   S   G   G   L 2360        2370        2380        2390        2400
GATTCCAGCCTGGTAACGGCGCTCGCCAGTCGTCATTTCAAAAAATTGAA
   D   S   S   L   V   T   A   L   A   S   R   H   F   K   K   L   N
```

Figure 4E

```
          2410        2420        2430        2440        2450
     TACGTATTCGATTGGTACGGAACTCAGCAATGAGTTTGAGTTTTCTCAAC
        T  Y  S  I  G  T  E  L  S  N  E  F  E  F  S  Q 2460        2470        2480        2490        2500
     AGGTTGCTGATGCACTCGGTACACATCATCAGATGAAAATTCTGTCCGAA
        Q  V  A  D  A  L  G  T  H  H  Q  M  K  I  L  S  E 2510        2520        2530        2540        2550
     ACTGAAGTGATCAACGGCATCATCGAATCCATCTATTACAACGAAATATT
        T  E  V  I  N  G  I  I  E  S  I  Y  Y  N  E  I  F 2560        2570        2580        2590        2600
     TGACGGCTTATCCGCTGAAATCCAATCCGGGTTGTTCAATGTCTATCGTC
        D  G  L  S  A  E  I  Q  S  G  L  F  N  V  T  R 2610        2620        2630        2640        2650
     AGGCTCAGGGGCAGGTGTCTTGCATGCTCACCGGATATGGTTCCGACCTG
        Q  A  Q  G  Q  V  S  C  M  L  T  G  Y  G  S  D  L 2660        2670        2680        2690        2700
     CTCTTTGGCGGCATACTGAAACCAGGAGCGCAGTATGACAATCCGAATCA
        L  F  G  G  I  L  K  P  G  A  Q  Y  D  N  P  N  Q 2710        2720        2730        2740        2750
     GCTGCTTGCCGAGCAAGTGTACCGGACGCGTTGGACAGGGGAGTTTGCTA
        L  L  A  E  Q  V  Y  R  T  R  W  T  G  E  F  A 2760        2770        2780        2790        2800
     CCCACGGTGCTTCCTGTTACGGCATTGATATTCGCCACCCCTTCTGGAGC
        T  H  G  A  S  C  Y  G  I  D  I  R  H  P  F  W  S 2810        2820        2830        2840        2850
     CATTCCCTAATCTCTCTATGTCATGCGCTACATCCTGATTACAAAATTTT
        H  S  L  I  S  L  C  H  A  L  H  P  D  Y  K  I  F 2860        2870        2880        2890        2900
     CGACAACGAAGTCAAAAACATCCTGCGTGAATACGCCGATTCGCTGCAAT
        D  N  E  V  K  N  I  L  R  E  Y  A  D  S  L  Q 2910        2920        2930        2940        2950
     TGCTGCCGAAAGACATTGTCTGGCGCAAGAAAATCGGCATTCACGAAGGT
        L  L  P  K  D  I  V  W  R  K  K  I  G  I  H  E  G
```

Figure 4F

```
           2960        2970        2980        2990        3000
      TCCTCCGTCAATCAGGCCTTTGCGAATGTTCTCGGGTCAACGGTTGATAA
       S   S   V   N   Q   A   F   A   N   V   L   G   S   T   V   D   N 3010        3020        3030        3040        3050
      CTACCAGACCAAAAGTCGCTTTACCTACCGTGTTTATCAAGCCTTCCTTC
        Y   Q   T   K   S   R   F   T   Y   R   V   Y   Q   A   F   L 3060        3070        3080        3090        3100
      GTGGCCGTCTCTCCATTACAGATGTGACGCCCTCTCAGCTTAAAGATCTG
       R   G   R   L   S   I   T   D   V   T   P   S   Q   L   K   D   L

EcoR1
           3110        3120        3130        3140        3150
      ATTAAAAAGGATTAATTATGGTTTTTGAAGAGAATTCCGATGAGGTCCGA
       I   K   K   D   *    M   V   F   E   E   N   S   D   E   V   R
                         CarB 3160        3170        3180        3190        3200
      GTGATCACGCTCGATCATCCGAACAAGCATAACCCCTTTAGTCGAACGCT
       V   I   T   L   D   H   P   N   K   H   N   P   F   S   R   T   L 3210        3220        3230        3240        3250
      GGAAACCAGCGTGAAGGACGCGCTGGCGCGAGCCAACGCTGACGACAGCG
        E   T   S   V   K   D   A   L   A   R   A   N   A   D   D   S 3260        3270        3280        3290        3300
      TACGAGCTGTCGTGGTGTATGGCGGGGCCGAGCGTTCCTTTTCCGCTGGC
       V   R   A   V   V   V   Y   G   G   A   E   R   S   F   S   A   G 3310        3320        3330        3340        3350
      GGAGATTTCAACGAAGTTAAGCAGCTATCGCGCAGCGAGGACATCGAAGA
        G   D   F   N   E   V   K   Q   L   S   R   S   E   D   I   E   E 3360        3370        3380        3390        3400
      GTGGATTGACCGCGTGATTGATTTGTATCAGGCCGTCCTGAATGTGAATA
        W   I   D   R   V   I   D   L   Y   Q   A   V   L   N   V   N 3410        3420        3430        3440        3450
      AACCGACGATCGCAGCGGTGGATGGCTATGCGATTGGTATGGGTTTCCAG
       K   P   T   I   A   A   V   D   G   Y   A   I   G   M   G   F   Q
```

Figure 4G

```
           3460       3470       3480       3490       3500
     TTCGCCCTGATGTTTGACCAGAGACTGATGGCGTCGACAGCAAATTTTGT
      F  A  L  M  F  D  Q  R  L  M  A  S  T  A  N  F  V 3510       3520       3530       3540       3550
     GATGCCGGAACTTAAGCATGGTATCGGGTGCTCGGTTGGGGCGGCCATTC
      M  P  E  L  K  H  G  I  G  C  S  V  G  A  A  I 3560       3570       3580       3590       3600
     TGGGATTCACCCACGGATTTAGCACAATGCAGGAAATCATCTACCAGTGC
      L  G  F  T  H  G  F  S  T  M  Q  E  I  I  Y  Q  C 3610       3620       3630       3640       3650
     CAGTCGCTCGATGCTCCACGCTGTGTGGACTACCGGCTGGTTAATCAGGT
      Q  S  L  D  A  P  R  C  V  D  Y  R  L  V  N  Q  V 3660       3670       3680       3690       3700
     GGTGGAGAGCAGTGCGCTGCTGGATGCCGCTATCACACAGGCGCACGTGA
      V  E  S  S  A  L  L  D  A  A  I  T  Q  A  H  V 3710       3720       3730       3740       3750
     TGGCTAGCTACCCGGCTTCTGCATTCATCAATACGAAACGAGCGGTTAAC
      M  A  S  Y  P  A  S  A  F  I  N  T  K  R  A  V  N 3760       3770       3780       3790       3800
     AAACCGTTCATCCATCTACTGGAACAAACCCGTGACGCTTCCAAAGCTGT
      K  P  F  I  H  L  L  E  Q  T  R  D  A  S  K  A  V 3810       3820       3830       3840       3850
     CCATAAGGCAGCGTTCCAGGCTCGTGACGCTCAGGGACATTTCAAAAATG
      H  K  A  A  F  Q  A  R  D  A  Q  G  H  F  K  N 3860       3870       3880       3890       3900
     TGCTTGGCAAAAAATACTGAGGATAAGGAAGAAAATGAGCGAAATAGTGA
      V  L  G  K  K  Y  *                carC M  S  E  I  V 3910       3920       3930       3940       3950
     AGTTTAATCCGGTCATGGCATCCGGTTTTGGCGCGTATATCGATCATCGG
      K  F  N  P  V  M  A  S  G  F  G  A  Y  I  D  H  R 3960       3970       3980       3990       4000
     GACTTTCTCGAAGCCAAGACAGAAACGATTAAAAACTTACTGATGCGTCA
      D  F  L  E  A  K  T  E  T  I  K  N  L  L  M  R  Q
```

Figure 4H

```
         4010        4020        4030        4040        4050
GGGATTTGTCGTGGTCAAAAATCTCGATATTGATAGTGACACATTCCGCG
  G   F   V   V   V   K   N   L   D   I   D   S   D   T   F   R 4060        4070        4080        4090        4100
ATATCTACTCGGCTTACGGTACGATCGTGGAGTATGCGGATGAAAAGATC
  D   I   Y   S   A   Y   G   T   I   V   E   Y   A   D   E   K   I 4110        4120        4130        4140        4150
GGCGTAGGTTTCGGCTATCGCGATACGTTGAAGCTGGAAGGGGAAAAAGG
  G   V   G   F   G   Y   R   D   T   L   K   L   E   G   E   K   G 4160        4170        4180        4190        4200
AAAAATCGTTACCGGACGTGGTCAACTTCCTTTCCACGCTGATGGCGGCC
  K   I   V   T   G   R   G   Q   L   P   F   H   A   D   G   G 4210        4220        4230        4240        4250
TGCTGCTGTCACAGGTAGATCAGGTTTTCCTCTACGCGGCCGAGATTAAA
  L   L   L   S   Q   V   D   Q   V   F   L   Y   A   A   E   I   K 4260        4270        4280        4290        4300
AACGTCAAATTCCGTGGTGCAACAACGGTATGCGACCATGCTCTGGCTTG
  N   V   K   F   R   G   A   T   T   V   C   D   H   A   L   A   C 4310        4320        4330        4340        4350
TCAGGAAATGCCGGCTCACCTTCTGCGCGTACTGGAAGAGGAAACGTTCG
  Q   E   M   P   A   H   L   L   R   V   L   E   E   E   T   F 4360        4370        4380        4390        4400
AAGTTCGTGTGCTAGAGCGGGGCTATTACGTGGATGTTTCACCAGACGGT
  E   V   R   V   L   E   R   G   Y   Y   V   D   V   S   P   D   G 4410        4420        4430        4440        4450
TGGTTCAAGGTGCCGGTCTTCACCGATCTGGGATGGGTCAGAAAGATGCT
  W   F   K   V   P   V   F   T   D   L   G   W   V   R   K   M   L 4460        4470        4480        4490        4500
GATTTATTTCCCATTTGACGAAGGACAACCGGCTAGCTGGGAGCCGCGGA
    I   Y   F   P   F   D   E   G   Q   P   A   S   W   E   P   R 4510        4520        4530        4540        4550
TTGTCGGTTTCACCGATCATGAAACCCAGGCATTCTTCCAGGAACTCGGG
  I   V   G   F   T   D   H   E   T   Q   A   F   F   Q   E   L   G
```

Figure 4I

```
         4560       4570       4580       4590       4600
GCGTTTTTAAAACAGCCACGCTACTACTACAAACACTTCTGGGAAGATGG
  A  F  L  K  Q  P  R  Y  Y  Y  K  H  F  W  E  D  G 4610       4620       4630       4640       4650
TGACCTGCTGATTATGGACAACCGTCGTGTCATTCATGAGCGTGAAGAGT
   D  L  L  I  M  D  N  R  R  V  I  H  E  R  E  E 4660       4670       4680       4690       4700
TTAACGATGACGACATCGTACGTCGTCTGTATCGCGGACAAACCGCCGAT
 F  N  D  D  D  I  V  R  R  L  Y  R  G  Q  T  A  D 4710       4720       4730       4740       4750
ATCTAACTCTCATGATTCCGGCGCGAAAACGTGCCGGATTGATATGGATC
  I  *

4760       4770       4780       4790       4800
TGGAACCATCATGCCTAACGATCTTTACGCTATCTACAATCGTTACACGT
       carD  M  P  N  D  L  Y  A  I  Y  N  R  Y  T 4810       4820       4830       4840       4850
CAAGGACCCTGTTTTTTAAATACTGTGCGACAGCGACGCTAACGCACAGA
 S  R  T  L  F  F  K  Y  C  A  T  A  T  L  T  H  R 4860       4870       4880       4890       4900
CTGACACGTCGGCTGTCGCTTTTTACGTTGAAAAAGTGCCTTGCCCGTCC
  L  T  R  R  L  S  L  F  T  L  K  K  C  L  A  R  P 4910       4920       4930       4940       4950
ACAGGGACGCCTTTTCTCTCTGGTTAATAGCATTTATTTTGGCGGAGAAA
   Q  G  R  L  F  S  L  V  N  S  I  Y  F  G  G  E 4960       4970       4980       4990       5000
CGCTGGAAGAGGTTCAGAGTACAGCAACTTTTCTGGCACGCTCTGGCATT
 T  L  E  E  V  Q  S  T  A  T  F  L  A  R  S  G  I 5010       5020       5030       5040       5050
GCTTGCGTACTGGACTACGCCGTGGAAGGGGAAAATGACGAGACGCAGTT
   A  C  V  L  D  Y  A  V  E  G  E  N  D  E  T  Q  F 5060       5070       5980       5990       5100
CGATAAGGCAATGGAAAATACGCTGCGCCTTATCGAGATGTCGCAGCAAA
    D  K  A  M  E  N  T  L  R  L  I  E  M  S  Q  Q
```

Figure 4J

```
       5110      5120      5130      5140      5150
CGGATAGCCTGCCTTTTGTCGTGATTAAACCGTCGTCTCTGGGTAGTGTT
 T  D  S  L  P  F  V  V  I  K  P  S  S  L  G  S  V 5160      5170      5180      5190      5200
GCTGTGTATGCTCGGCAAAGTGAAAGGCTCGCGCTGGATGAAGCATCCGC
 A  V  Y  A  R  Q  S  E  R  L  A  L  D  E  A  S  A 5210      5220      5230      5240      5250
CAGCGCATGGTCACGCATCGTTACGCGTTTCTCACGTCTGTTCGATTATG
 S  A  W  S  R  I  V  T  R  F  S  R  L  F  D  Y 5260      5270      5280      5290      5300
CCCGCTCTCATGGCGTGCATGTGATGGTTGATGCAGAGCAGACCGCGATT
 A  R  S  H  G  V  H  V  M  V  D  A  E  Q  T  A  I 5310      5320      5330      5340      5350
CAGCCCGCAGTGGATCGTTTGGTTCTAGACATGATGCGTGAATTTAACCG
 Q  P  A  V  D  R  L  V  L  D  M  M  R  E  F  N  R 5360      5370      5380      5390      5400
CGATAGCGCGGTGATCACGCTGACGCTGCAATTTTATCTAAAGGATCAAT
 D  S  A  V  I  T  L  T  L  Q  F  Y  L  K  D  Q 5410      5420      5430      5440      5450
TGCGTTTTCTCGACGAATGCTATCAGCGAGCCTGTCAGGATAATTTCCTG
 L  R  F  L  D  E  C  Y  Q  R  A  C  Q  D  N  F  L 5460      5470      5480      5490      5500
TTCGGCGTGAAAGTAGTGCGCGGTGCTTATCTGGAAGAAGAGAAACGAGT
 F  G  V  K  V  V  R  G  A  Y  L  E  E  E  K  R  V 5510      5520      5530      5540      5550
GAACGGTGGCGTACGCTGTTTTGCAACCAAACAGGAAACCGATCGTAGTT
 N  G  G  V  R  C  F  A  T  K  Q  E  T  D  R  S 5560      5570      5580      5590      5600
ATAACGCGGCGGTGGATTACATTGCACTGCGTCTGGATCGAATCGCACCG
 Y  N  A  A  V  D  Y  I  A  L  R  L  D  R  I  A  P 5610      5620      5630      5640      5650
TTTTTCGCCACGCACAACGAGGAAAGCCTCGCTTTGATTATGTCGAGTGA
 F  F  A  T  H  N  E  E  S  L  A  L  I  M  S  S  E
```

Figure 4K

```
       5660        5670        5680        5690        5700
GTCGCTACGCGCGGGGCGCACCTGGGTAGGCCAGCTTTACGGGTTGGGCG
  S   L   R   A   G   R   T   W   V   G   Q   L   Y   G   L   G 5710        5720        5730        5740        5750
ATCATATTACTTATTCGCTGCTGCAAACCGGTTTCCGCGTGTGCAAATAC
 D   H   I   T   Y   S   L   L   Q   T   G   F   R   V   C   K   Y 5760        5770        5780        5790        5800
CTGCCTTACGGTCCGCTCGATAAGTCGTTGCCCTATTTACTCCGCAGGAT
  L   P   Y   G   P   L   D   K   S   L   P   Y   L   L   R   R   I 5810        5820        5830        5840        5850
TGAAGAGAACGCGGTTGCCTCGGCAACCTTCAAAAAGGAAAATAAACTCT
   E   E   N   A   V   A   S   A   T   F   K   K   E   N   K   L 5860        5870        5880        5890        5900
TGCAGAAGGAGTTGCTGCGCCGTCTCGTAGGAGGGATGTAATGTCAAAAT
  L   Q   K   E   L   L   R   R   L   V   G   G   M   *
                                                   CarE  M   S   K   F 5910        5920        5930        5940        5950
TTCATTGTCATATTCGCGATACGGCTATCGGTTTCCCCGTGTCGGAGGAT
  H   C   H   I   R   D   T   A   I   G   F   P   V   S   E   D   E 5960        5970        5980        5990        6000
GAAAGCGTACTCAGTTCAGCCTATGAAGCTGGTGTCGAACTGCCTTATCG
   S   V   L   S   S   A   Y   E   A   G   V   E   L   P   Y   R 6010        6020        6030        6040        6050
CTGTGCTTCTGGTTACTGTGGTGTATGCAAGGTGCGCCTGACGTCCGGCA
 C   A   S   G   Y   C   G   V   C   K   V   R   L   T   S   G   N 6060        6070        6080        6090        6100
ACGTCAACATGGATCATTCTGGTGGGATCTCACGTAAAGATATCGCTGAT
   V   N   M   D   H   S   G   G   I   S   R   K   D   I   A   D   G 6110        6120        6130        6140        6150
GGTTACATTCTACCTTGCTGTTCTGTGCCGCTCTCTAACCTCGAAATTGA
    Y   I   L   P   C   C   S   V   P   L   S   N   L   E   I   E
```

Figure 4L

```
         6160       6170       6180       6190       6200
ACCTGTATCGTCATGCTGAAGAAAACGCTAATTGTTGGACTGTGCTGTAC
   P   V   S   S   C   *
             carF  M   L   K   K   T   L   I   V   G   L   C   C   T 6210       6220       6230       6240       6250
TTTCCCCCTCTTCTCCGCTCAAGCGGTGAATACTGTTCCTGACGAGGTGG
   F   P   L   F   S   A   Q   A   V   N   T   V   P   D   E   V 6260       6270       6280       6290       6300
TTGTCAAAGGTGGCAATTTCTATGTTGGATCGGTCTTCGGCTCGGAAGAC
   V   V   K   G   G   N   F   Y   V   G   S   V   F   G   S   E   D 6310       6320       6330       6340       6350
TATGCTGCTCATGCCAACACGTCTATCGCGTCTTTTGCCATCACGAAAAC
   Y   A   A   H   A   N   T   S   I   A   S   F   A   I   T   K   T 6360       6370       6380       6390       6400
GGAAATTACCTATCGGCAGTATCATGCGTTGCAAGAATGGGCGGACACAC
   E   I   T   Y   R   Q   Y   H   A   L   Q   E   W   A   D   T 6410       6420       6430       6440       6450
ACGGTTATGAGCTTAGTGGCGGCTGCAATGGCGCGACTTTCGAAGATTGC
 H   G   Y   E   L   S   G   G   C   N   G   A   T   F   E   D   C 6460       6470       6480       6490       6500
TTACCGCCTGAACAGGATAACAGTCTTCATCCTGTCACGAATGTATCTTG
   L   P   P   E   Q   D   N   S   L   H   P   V   T   N   V   S   W 6510       6520       6530       6540       6550
GTGGGATGCAGTGATTTTTGCCAATGTGCTCAGTGAACGGCAGCAGTTGC
   W   D   A   V   I   F   A   N   V   L   S   E   R   Q   Q   L 6560       6570       6580       6590       6600
AGCCCTATTACCTCACGATTGACGGTAAGACGCTGAAACGCGTGCCGGAG
   Q   P   Y   Y   L   T   I   D   G   K   T   L   K   R   V   P   E 6610       6620       6630       6640       6650
GACGATAACGATAAACTCATACGCGAGAACCCGCAGGCTTTGGGGTATCG
   D   D   N   D   K   L   I   R   E   N   P   Q   A   L   G   Y   R 6660       6670       6680       6690       6700
CTTGCCGACGCTGGCGGAATGGCAAGTGGCAGCCAGAGGCGGAAAGAAGG
   L   P   T   L   A   E   W   Q   V   A   A   R   G   G   K   K
```

Figure 4M

```
        6710       6720       6730       6740       6750
GGCTGGCGCAGGGGACGTACGGACAGCGCTATGCCGGTAGCGAACAGCCG
  G  L  A  Q  G  T  Y  G  Q  R  Y  A  G  S  E  Q  P 6760       6770       6780       6790       6800
GACAGTGTGGCGCATTTTCCTTCTGACTCTCAATCATTCGGCACGGTGCC
  D  S  V  A  H  F  P  S  D  S  Q  S  F  G  T  V  P 6810       6820       6830       6840       6850
TGTGACCTCGAAGCGCCCCAATGCTCTGGGGCTTTACGATATGAGTGGCA
   V  T  S  K  R  P  N  A  L  G  L  Y  D  M  S  G 6860       6870       6880       6890       6900
ATGTATCCGAGTGGCTGAATGAGTCTTATGCGGTGGAAGGCGGCAAAACC
  N  V  S  E  W  L  N  E  S  Y  A  V  E  G  G  K  T 6910       6920       6930       6940       6950
ATGTACTACTTTTGCGGCGGAAGTTATCTGGAACGCACGCACAGTCTTGC
  M  Y  Y  F  C  G  G  S  Y  L  E  R  T  H  S  L  A 6960       6970       6980       6990       7000
TAGCTGCGATCTGCATACGCCCGGTTTTTTCATGCCGGATATTGGTTTTC
   S  C  D  L  H  T  P  G  F  F  M  P  D  I  G  F 7010       7020       7030       7040       7050
GACTAGTAAGGACACTTGATGGTCAATAAGTTCGTAGGGTGGCTGGCGCT
  R  L  V  R  T  L  D  G  Q  *
                CarG  M  V  N  K  F  V  G  W  L  A  L 7060       7070       7080       7090       7100
CTGTGCCATTAGCAACACGGCTGCTGCACTCTCTCCTGTGACATTGAAAG
   C  A  I  S  N  T  A  A  A  L  S  P  V  T  L  K 7110       7120       7130       6740       7150
ACGGCATCAATCGGCTGGATCTCAATCAGGGCGGCGGGAACGATTATGTC
  D  G  I  N  R  L  D  L  N  Q  G  G  G  N  D  Y  V 7160       7170       7180       7190       7200
GTTGTTGCCCAATTTGACAACAATACCTCGCATCCTAATCTCGGGATGAC
  V  V  A  Q  F  D  N  N  T  S  H  P  N  L  G  M  T 7210       7220       7230       7240       7250
CTTTTTTGTCCGCCGTCCAGACGGTGGGCATAGCATTATGCCGGTAGCCA
   F  F  V  R  R  P  D  G  G  H  S  I  M  P  V  A
```

Figure 4N

```
         7260       7270       7280       7290       7300
    ACAGCAATACGTTTACCTGGTTCGACTATCGCCTGTCCGCTGCGGCGGAT
      N  S  N  T  F  T  W  F  D  Y  R  L  S  A  A  A  D 7310       7320       7330       7340       7350
    TTTCTGGTGCAGGACAATCGGCTATTCCTGTCTGGAAAGCATTACTTTCT
      F  L  V  Q  D  N  R  L  F  L  S  G  K  H  Y  F  L 7360       7370       7380       7390       7400
    GGTGACGGCACGGAAGCAGGGTGAAAACGTCTTTGATCCCACAAAAGTCG
      V  T  A  R  K  Q  G  E  N  V  F  D  P  T  K  V 7410       7420       7430       7440       7450
    TTTTAACAATTTACGACTTTAAAGCCTCACGGGACGATCCCGGTGTACCA
      V  L  T  I  Y  D  F  K  A  S  R  D  D  P  G  V  P 7460       7470       7480       7490       7500
    CTCTATGAATGGTCGGAGCGCAAGCGTGTGGTAACACAAGATACCTACCA
      L  Y  E  W  S  E  R  K  R  V  V  T  Q  D  T  Y  Q 7510       7520       7530       7540       7550
    ATCGGTCGATGAGGCCTACAAGGAAGTGAATGAGGCGATGCTGGCAAAAT
      S  V  D  E  A  Y  K  E  V  N  E  A  M  L  A  K
                                                    carH M 7560       7570       7580       7590       7600
    GAAAATATCGGTATTAATCGCATCCGGGCTATTGGCATCTTTCGGGGCGT
    *
         K  I  S  V  L  I  A  S  G  L  L  A  S  F  G  A 7610       7620       7630       7640       7650
    GGGCGCAACTCAGTGAGCAGGATTACCAGCAACGCGTACAGGAGTTTTTT
      W  A  Q  L  S  E  Q  D  Y  Q  Q  R  V  Q  E  F  F 7660       7670       7680       7690       7700
    GATGCAGAACCGCCGCTGTGTCTGGGCGAGAAGCAGTGGCCGGTTCATAG
      D  A  E  P  P  L  C  L  G  E  K  Q  W  P  V  H  S 7710       7720       7730       7740       7750
    TCCCAAAGGTGATTCTCCCTGGAACAGTGGACGGTTGCATACGCTTGTGG
        P  K  G  D  S  P  W  N  S  G  R  L  H  T  L  V
```

Figure 40

```
         7760       7770       7780       7790       7800
     AAGCGGGGTTGGCATACGCGACGCCTGAAGGAACAGGAAAGGTATATCGG
      E  A  G  L  A  Y  A  T  P  E  G  T  G  K  V  Y  R 7810       7820       7830       7840       7850
     TTATCGCCTGTAGGTGAGAAGAATTGGCGTCAACATGGCGACCTTTGCTA
      L  S  P  V  G  E  K  N  W  R  Q  H  G  D  L  C  Y 7860       7870       7880       7890       7900
     TGGCCGTATGCAAGTGAGCCGTATTGAGAAATCGATCGTGTGAACCAGG
       G  R  M  Q  V  S  R  I  E  K  I  D  R  V  N  Q 7910       7920       7930       7940       7950
     AACTGACGGTAGTGTATTTCACTTATCATCTGACATCGTTGGAAAGTTGG
      E  L  T  V  V  Y  F  T  Y  H  L  T  S  L  E  S  W 7960       7970       7980       7990       8000
     GCTCATAACCGTTCGTTACGCTTTGCTTTTAGCGAGTTGGATAATCTTGT
      A  H  N  R  S  L  R  F  A  F  S  E  L  D  N  L  V 8010       8020       8030       8040       8050
     CGGTGGAATGGAAACCACGCGTTATTCCGCTACGATTCGTGAGACGTTGG
       G  G  M  E  T  T  R  Y  S  A  T  I  R  E  T  L 8060       8070       8080       8090       8100
     GCGGGGCGGCCAAATTGCAGGATTACCCCGTGCCGGTAGAGCTGGATTAC
      G  G  A  A  K  L  Q  D  Y  P  V  P  V  E  L  D  Y 8110       8120       8130       8140       8150
     TAATCTGAAATCTTATTGACGTGACATAAAAAAAACAGGGTGAACGTGGT
      *

8160       8170       8180       8190       8200
     TCACCCTGCTGCATTTTACTGTCTTGGCGTGACGCCAGAGGGGATTAGCG 8210       8220       8230       8240       8250
     TAAATCCAGCATCGCGATATGGTCCATATCGTCAAACGTTAGGTTTTCGC 8260       8270       8280       8290       8300
     CGATCATGCCCCAGATAAAGGCATAGTTTTTGGTGCCGACACCGGTGTGA

NsiI
         8310       8320       8330       8340
     ATCGACCAACTCGGGGAGATCACGGCCTGCTCGTTATGCAT
```

GENES INVOLVED IN THE BIOSYNTHETIC PATHWAY OF CARBAPENEM

This application was filed under 35 U.S.C. 371 from PCT/GB95/01125 filed May 18, 1995.

FIELD OF THE INVENTION

The present invention relates to the bacterial gene expression of carbapenem antibiotics.

BACKGROUND OF THE INVENTION

The carbapenem antibiotics constitute a diverse group of β-lactam antibiotics characterised by potent anti-bacterial and β-lactamase-resistant activity. More than forty different carbapenems are known, most of which are produced by the actinomycetes, particularly *Streptomyces spp* (Ratcliffe and Albers-Schonberg, 1982; Brown 1984; Williamson 1986; all cited in Baiton et al 1992).

Carbapenems have been isolated from the Gram-negative bacterium *Serratia marcescens* and *Erwinia carotovora* by Parker et al. (1982) and in *Azospirillum spp* UK 1521 by Kintaka et al. (1985); all cited in Bainton et al 1992.

Bainton et al (1992) have recently shown that carbapenem biosynthesis is regulated by the regulatory factor N-(3-oxohexanoyl)-L-homoserine lactone (known as HSL or OHHL). This compound was previously only known for its role in auto-induction of bioluminescence in the marine bacterium *Vibrio fischeri*. OHHL is also structurally related to the A- and I-factors which are known to regulate production of antibiotics in some Streptomyces species.

BRIEF DESCRIPTION OF THE DRAWINGS

FIG. 4 shows the entire nucleotide and predicted amino acid sequence of carR, carA, carB, carD, carE, carF, carG and carH.

DETAILED DESCRIPTION OF THE INVENTION

Figure 1:
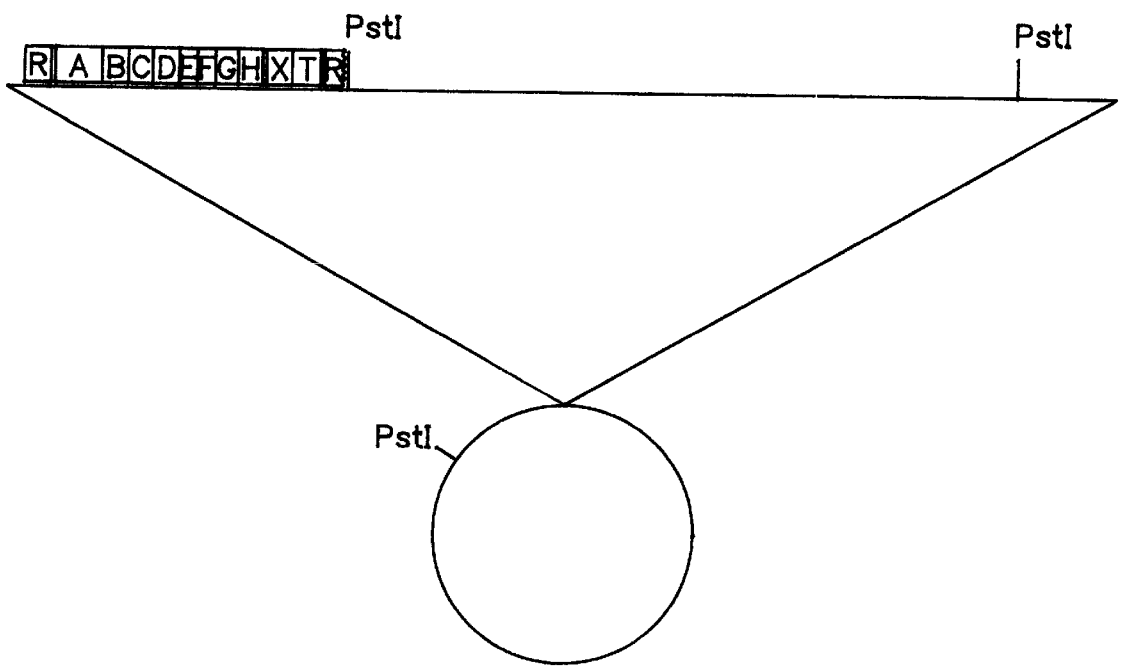
FIG. 1 shows the cosmid cWU142 and the organization of the car genes R,A,B,C,D,E,F,G,H.

In order to examine the biosynthetic and regulatory mechanism involved in the production of the β-lactam antibiotic 1-carbapen-2-em-3-carboxylic acid by *Erwinia carotovora*, blocked mutants were obtained with a carbapenem non-producing phenotype (Car ) as described by Bainton et al (1992). These mutants fell into two distinct groups: group 1 mutants secreted a low molecular mass diffusible factor which restored carbapenem biosynthesis in group 2 mutants, but not vice versa. This factor was shown to be OHHL. Class 1 mutants produced OHHL and were thus thought to be defective in carbapenem biosynthetic genes.

In order to study class 1 mutants a chromosomal DNA cosmid library of *Erwinia carotovora* strain ATCC 39048 was constructed in *Escherichia coli*. The cosmids produced were used in standard complementation studies to find a sequence which could restore the carbapenem antibiotic production in the class 1 mutants.

One cosmid (cWU142) was presumed to contain the carbapenem biosynthetic genes. Restriction fragments of this cosmid were sub-cloned and a 3.8 Kb EcoRI fragment was found to complement 7 out of 8 class 1 mutants. This fragment was sequenced and shown to comprise 2 Kb of cosmid DNA and 1.8 Kb of Erwinia DNA. This was extremely unexpected because known antibiotic biosynthetic gene sequences are much longer than 1.8 Kb.

The 1.8 Kb gene sequence was found to encode CarR, a homologue of the LuxR regulatory protein from the Lux operon system associated-with the bioluminescence phenotype of the marine bacterium *V. fischeri*.

In *V. fischeri* OHHL synthesis is coded for by the gene luxI. In *Erwinia carotovora*, OHHL synthesis is encoded by a luxI homologue which has been named carI.

By analogy with the *V. fischeri* Lux system, the inventors postulated that when OHHL is made, it binds to CarR which can then act as a transcriptional activator of the carbapenem biosynthetic genes. Thus, the inventors reasoned that 7 out of 8 of the class 1 mutants are not, as expected, defective in genes required for synthesis of carbapenem, but in a gene encoding a regulatory protein CarR, needed to switch on the carbapenem biosynthesis genes. Without the carR gene product the carbapenem biosynthetic genes are not expressed, that is, they remain silent or cryptic.

Our co-pending application GB-9311641.6 relates to the carR gene product and to DNA sequences encoding it.

We therefore used direct cosmid complementation of a strain of class 1 mutants (strain PNP 14) to clone a complementing cosmid (cWU142). We presumed that this would carry all the biosynthetic genes. When cWU142 was transferred into other class 1 mutants it complemented all of them. cWU142 did not complement any class 2 mutants (this is because the carI gene is physically separate from the biosynthetic genes). We showed that the cWU142 cosmid carries the gene (carR) encoding the LuxR homologue. The CarR protein acts as a positive activator of the car biosynthetic genes and functions in trans. This carR gene is capable of activation of carbapenem antibiotic production in several other Erwinia strains (approx. 18–20% of random strains). One of the class 1 mutants (PNP21) was not complemented by the carR gene alone and was presumed to be a real biosynthetic mutant. cWU142 complemented this mutant, implying that the car biosynthetic genes were indeed on the cosmid. This was confirmed by the observation that, in *E. coli*, cWU142 could encode carbapenem synthesis simply by the exogenous addition of chemically-synthesised OHHL. It seems that the car biosynthetic genes are not expressed because the CarR protein requires activation by the OHHL although the requirement for OHHL can be over-ridden by producing CarR in high dosage e.g. by providing the carR gene in trans on a multicopy plasmid. In *Erwinia carotovora* there is endogenous OHHL so the car genes are switched on.

Thus all genes for antibiotic production and one for regulation (carR) were on cWU142, permitting the carbapenem antibiotic biosynthetic pathway to be reconstituted in a heterologous organism (in this case *E. coli*).

The cWU142 cosmid was subcloned to produce smaller plasmids which still express the antibiotic. Plasmid pSMG12 encoded antibiotic synthesis in *E. coli* in the presence of exogenously added OHHL. Plasmid pSMG13 was engineered to contain the carI gene in addition to the genes found in pSMG12. Plasmid pSMG13 encoded carbapenem production without the need for exogenously added OHHL. This strain makes OHHL (from the carI gene product) and apparently acts with CarR to transcriptionally activate the carbapenem biosynthetic genes. Further subcloning of the pSMG13 plasmid has shown that the cluster of 9 genes carR,carA,carB,carC,carD,carE,carF,carG,carH is sufficient to express carbapenem in E. coli if OHHL is added. OHHL is not required if the carI gene is also present and functional. All of the Erwinia DNA in the pSMG12/pSMG13 plasmid has been sequenced to define the genes carR to carH.

According to one aspect of this invention we provide, either separately or in combination, DNA comprising the genes carA,carB,carC,carD,carE,carF,carG,carH.

Preferably, we provide DNA comprising at least the CarA, CarB and CarC genes. More preferably we provide DNA comprising the CarA, CarB, CarC, CarD and CarE genes. Also included within the invention are DNA capable of hybridising to any of the DNAs defined above and capable of functioning as such DNAs in the carbapenem biosynthetic pathway, and DNAs which are equivalent by virtue of the degeneracy of the genetic code.

The CarF and CarG genes are now known to be involved in conferring resistance to the antibiotic produced by the organism.

The DNA may also include either or both of the regulatory genes carI and carR.

The DNA according to the invention may comprise genes of *Erwinia carotovora,* or DNA capable of hybridising to any of said genes and capable of functioning as such genes in the biosynthetic pathway of a carbapenem.

Such hybridising DNA may comprise native genes from other carbapenem-synthesising organisms or partially or wholly synthetic DNA.

We also provide DNA which is equivalent to any DNA mentioned above by virtue of the degeneracy of the genetic code.

Portions of the *Erwinia carotovora* genes or corresponding genes from other organisms are included provided that such portions can function in carbapenem synthesis.

We also provide a polypeptide coded for by DNA as defined hereinabove.

We further provide a recombinant DNA molecule including any DNA as defined hereinabove.

We also provide a recombinant DNA molecule, including the cluster of genes carA,carB,carC,carD, carE,carF,carG, carH. Such a recombinant DNA molecule may also contain either or both of the regulatory genes carR and carI, or may be placed under the control of a heterologous regulated promoter. The recombinant DNA molecule is preferably an expression vector capable of expressing a carbapenem coded for by said gene cluster.

In such a recombinant DNA molecule, any of the above-mentioned genes may be replaced by DNA capable of hybridizing thereto and which is itself capable of functioning in the carbapenem biosynthetic pathway.

Any of the above-mentioned genes may be replaced by DNA which is equivalent to it by virtue of the degeneracy of the genetic code.

Examples of recombinant DNA molecules as mentioned above are the cosmid cWU142 and plasmids pSMG12 and pSMG13.

We also provide a method of identifying further DNA coding for production of a carbapenem by using a DNA sequence as defined hereinabove, and preferably at least a substantial part of one or more of the genes carR carA,carB, carC,carD, caE,carF,carG,carH as a hybridization probe, incorporating any further DNA so identified into an expression vector, transforming a host with the resulting recombinant expression vector, expressing the polypeptide coded for by said further DNA, and testing said polypeptide for carbapenem biosynthetic activity.

The known carbapenem genes or portions thereof may thus be used to search for homologues in other bacteria as well as other organisms such as fungi. The procedure is particularly appropriate for searching for carbapenem gene homologues in streptomycetes producing Thienamycin and other carbapenems. The portions of the above-mentioned genes to be used as hybridization probes may if necessary be modified by replacing codons by codons coding for the same amino acids but more appropriate to the organism under investigation.

The *Erwinia carotovora* strain used throughout was *Erwinia carotovora* subspecies carotovora (ATCC39048).

An internal StuI fragment from the car cluster of the strain of *Erwinia cartovora* described above (containing DNA internal to carA through to a site internal to carG) was used to probe chromosomal DNA from various other *Erwinia carotovora* strains. Of 16 strains probed, 10 yielded positive hybridisation signals. The StuI probe was also used to probe DNA from other *Erwinia carotovora* subspecies, and bacteria of other genera, namely *Serratia marcescens* and *Streptomyces cattleya*. Positive signals were seen with *Erwinia carotovora* subspecies atroseptica (strain SCRI39), *Erwinia carotovora* subspecies betavasculorum (strain SCRI479), *Serratia marcescens* (ATCC39006) and *Streptomyces cattleya* (strain 8057). We therefore believe that those strains showing positive hydridisation signals carry genes homologous to the car genes of our original strain (ATCC39048). In fact we have established that *Serratia marcescens* (ATCC39006) produces exactly the same antibiotic as the original *Erwinia carotovora* strain. We have determined the sequence of the complete Car cluster from *Serratia marcescens* (ATCC39006) and all of the genes are highly homologous to the corresponding genes of *Erwinia carotovora* (ATCC39048).

We have also performed PCR amplificiation of carC homologues in *Streptomyces cattleya.* The rationale for this is that antibiotic synthesis (and resistance) genes are usually clustered in bacteria and so cloning part of any one gene in the Streptomyces cluster then provides a “probe” with which to clone the rest of the cluster.

In addition to knowing the total car cluster sequence from *Erwinia carotovora,* we also cloned and sequenced the homologous sequences from *Serratia marcescens* (strain ATCC39006). As with the Erwinia cluster, the equivalent car cluster from Serratia also encodes carbapenem synthesis when cloned in *E. coli.* Two 18mer oligonucleotide primers were designed based on totally conserved amino acids in the predicted protein sequence of the *Erwinia carotovora* and *Serratia marcescens* carC genes (strep-C1 and strep-C2).

Oligonucleotide Primer Sequences

Strep-C1 CCG C/GGA CAT CTA CTC C/GGC (SEQ. ID NO:11)

Strep-C2 CCG TCC TCC CAG AAG TGC (SEQ. ID NO:12)

The two conserved regions chosen spanned DNA encoding 185 amino acids of the predicted Erwinia gene product. In order to bias the primers for use with Streptomyces DNA, which has a high ratio of G and C residues, the amino acid sequence was back translated using G and C residues where possible. This resulted in the oligonucleotides being of mixed sequence where the amino acid could be encoded by more than one DNA sequence.

PCR reactions were performed using the above primers. A number of sets of reactions were performed with varying concentrations of template DNA, primer DNA, dNTPs and magnesium chloride. The denaturing time, annealing temperature and ramp rate of the PCR programme were also varied.

A PCR product of approximately 500 base pairs was seen in some of the reactions using the primers strep-C1 and strep-C2 and the *Streptomyces cattleya* DNA as template.

The carA to carH gene products may be used to make antibodies for use in identifying in a library streptomycete clones expressing a cross-reacting protein. This is a possible route to the identification of new car genes and new carbapenem antibiotics.

EXAMPLES

Figure 2:
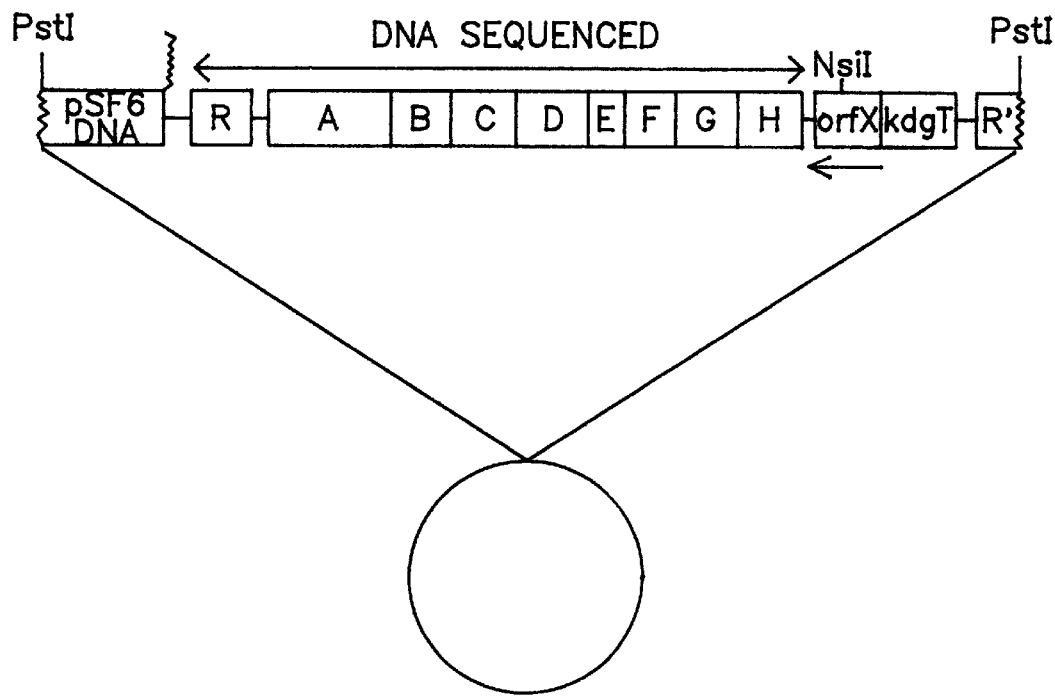
FIG. 2 shows plasmid pSMG12.

The cloning of the carbapenem biosynthetic genes will now be described in more detail and with reference to the accompanying figures, by way of example only:

FIG. 1 shows schematically the cosmid cWU142, showing the organisation of the car genes R,A,B,C,D,E,F,G,H, as well as unrelated genes (X,T,R') and the three PstI restriction sites. Cosmid cWU142 was obtained by cloning the carbapenem biosynthetic genes into the low copy number plasmid pSF6.

cWU142 was digested with PstI, to yield three large (ie greater than 12 kb) fragments. Each of these three fragments was cloned individually in pUC9. The clone that was shown by PCR analysis to contain carR was named, pSMG10. The fragment within this construct was subsequently recloned using PstI in pACYC177 and this construct was named pSMG12 (FIG. 2).

Figure 3:
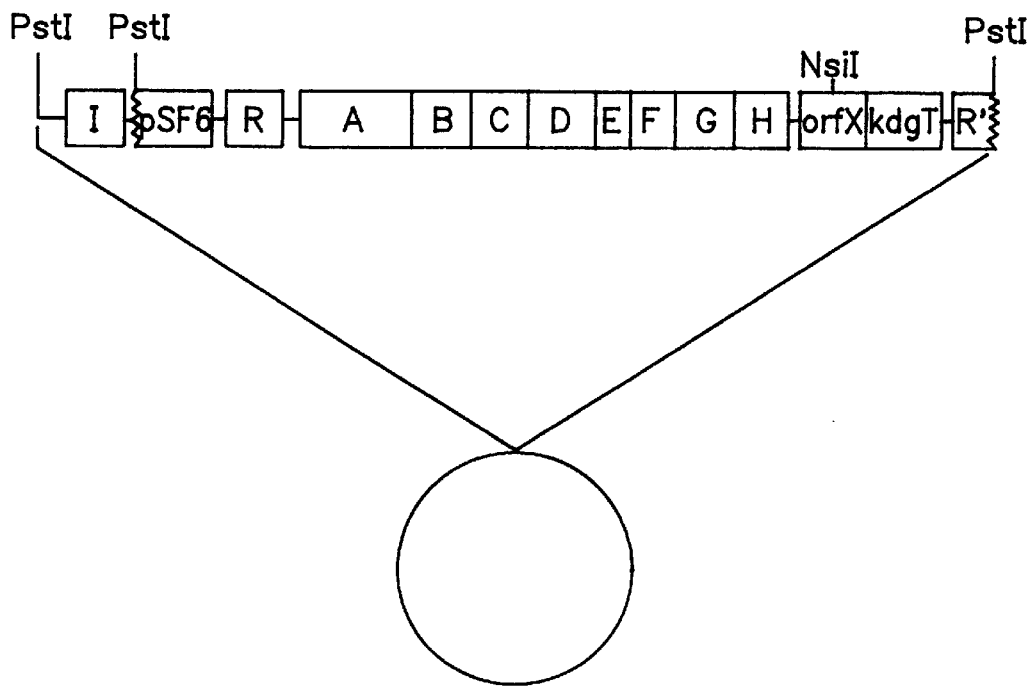
FIG. 3 shows plasmid pSMG13.

The carI gene had previously been cloned in pSJ10 and been shown to be present on a 2.3 kb PstI fragment (S. Jones). This carI containing fragment was cloned into pSMG12 following partial digestion of this plasmid with PstI. The resulting construct was named pSMG13 (FIG. 3).

*E. coli* containing plasmids pSMG12 or pSMG13 was spotted onto a lawn of the carbapenem hyper-sensitive strain of *E. coli* ("Beecham's *E. coli*"). A zone of clearing around the pSMG13-containing strain indicated the production by this strain of carbapenem. When exogenous N-(3-oxohexanoyl)-L-homoserine lactone (OHHL) was added to both strains, then the pSMG12 carrying strain could also produce carbapenem.

FIG. 4 shows the entire sequence of the carR,carA,carB, carC,carD,carE,carF,carG,carH genes, together with the sequences of the polypeptides that they encode. The sequences of some upstream and downstream DNA are also shown, including a portion of the orfX gene which, like the adjacent kdgT and $R^1$-genes do not form part of the carbapenem biosynthetic pathway.

From complementation and cross feeding studies, involving the mutants and cosmids of both *Serratia marcescens* (Sma) and Erwinia carotovora subspecies cartovora (Ecc) it appeared that all the genes necessary for carbapenem biosynthesis were also contained on 2 Sma cosmids, pNRT1 and pNRT20. These Sma carbapenem cosmids seemed to be functionally interchangeable in many cases with the Ecc cosmid cWU142, and it seemed likely that putative carbapenem genes might be quite highly conserved between the two genera. Southern blot hybridisations were used to localise the carbapenem gene region on the cosmids and this facilitated the subcloning and sequencing of the Sma carbapenem genes. 8.7 kb from the Sma carbapenem gene region was sequenced and was found to contain 9 ORFs, carRABCDEFGH, all transcribed in the same direction, with carABCDEFGH possibly forming an operon. The 9 genes had both similar size and high DNA homology to the 9 genes sequenced from the carbapenem gene region of Ecc. The predicted gene products also showed high amino acid sequence homology with the corresponding gene products from Ecc.

---

We claim:
1. A DNA fragment comprising:
(a) at least one of the genes carA, carB, carC, carD, carE, carF, carG, carH, as defined in FIG. 4;
(b) DNA which specifically hybridizes to any of the genes defined in (a) and which encodes polypeptides which function in the biosynthetic pathway of a carbapenem;
(c) DNA encoding polypeptides having the same amino acid sequence as polypeptides encoded by the DNA defined in either (a) or (b) above, by virtue of the degeneracy of the genetic code.
2. A DNA fragment comprising:
(a) the cluster of at least genes carA, carB, and carC as defined in FIG. 4;
(b) DNA which specifically hybridizes to the genes defined in (a) and which encodes polypeptides which function in the biosynthetic pathway of a carbapenem;
(c) DNA encoding polypeptides having the same amino acid sequence as polypeptides encoded by the DNA defined in either (a) or (b) above, by virtue of the degeneracy of the genetic code.
3. A DNA fragment comprising:
(a) the cluster of genes carA, carB, carC, carD, and carE as defined in FIG. 4;
(b) DNA which specifically hybridizes to the genes defined in (a) and which encodes polypeptides which function in the biosynthetic pathway of a carbapenem;
(c) DNA encoding polypeptides having the same amino acid sequence as polypeptides encoded by the DNA defined in either (a) or (b) above, by virtue of the degeneracy of the genetic code.
4. A DNA fragment according to any one of claims 1, 2 or 3, also containing either or both of the regulatory genes carR, as defined in FIG. 4, and carI.

5. A DNA fragment as defined in any one of claims 1, 2 or 3, wherein the gene is a gene of *Erwinia carotovora*.

6. A DNA fragment as defined in any one of claims 1, 2 or 3, wherein said DNA comprises one or more native genes from a carbapenem encoding organism or partially or wholly synthetic DNA.

7. A polypeptide coded for by a DNA fragment as defined in claim 1.

8. A recombinant DNA molecule including a DNA fragment as defined in claim 1.

9. A recombinant DNA molecule according to claim 8, including the cluster of genes carA, carB, carC, carD, carE, carF, carG, carH.

10. A recombinant DNA molecule according to claim 8 or 9 which also contains either or both of the genes carI and carR.

11. A recombinant DNA molecule according to claim 2 which is an expression vector capable of expressing a carbapenem polypeptide coded for by said gene cluster.

12. A method identifying a DNA encoding a polypeptide functioning in the production of a carbapenem by using a DNA fragment as defined in claim 1 or a portion of such a DNA fragment as a specific hybridization probe, incorporating any DNA so identified into an expression vector, transforming a host cell with the resulting recombinant expression vector, expressing the polypeptide coded for by said DNA, and testing said polypeptide for carbapenem production activity.

13. A method according to claim 12, wherein said DNA is amplified by means of PCR.

14. A method for identifying a DNA encoding a polypeptide functioning in the production of a carbapenem by using a DNA fragment as defined in claim 4 or a portion of such a DNA fragment as a specific hybridization probe, incorporating any DNA so identified into an expression vector, transforming a host cell with the resulting recombinant expression vector, expressing the polypeptide coded for by said DNA, and testing said polypeptide for carbapenem production activity.

15. A DNA identified by the method of claim 12.

16. A recombinant DNA vector incorporating DNA as defined in claim 15.

17. A polypeptide coded for by DNA as defined in claim 15 or by a recombinant DNA vector as defined in claim 16.

* * * * *

UNITED STATES PATENT AND TRADEMARK OFFICE
CERTIFICATE OF CORRECTION

PATENT NO. : 5,871,922
DATED : 2/16/99
INVENTOR(S) : Salmond et al.

It is certified that error appears in the above-identified patent and that said Letters Patent is hereby corrected as shown below:

Column 1, line 39, "Fig. 4 shows" should read --Figs 4(A)-4(O) show--.

Signed and Sealed this

Fourth Day of May, 1999

*Attest:*

Q. TODD DICKINSON

*Attesting Officer*  Acting Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 8341 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Erwinia carotovora ( x i ) SEQUENCE DESCRIPTION: SEQ ID NO: 1:

```
AGATCGGCGC   ACTGCGTGCC   TTTGGCGACG   CCGCGTTACG   GCATTTTCAC   GCTGATTTGG        60

AGCGGGCTGA   TGTCGCTGGT   GAGCGTCGGC   GTGCTGCTGG   GTGTCGGTCT   GGGCTACCTT       120

GCCGCCCGCG   CGATTGCGGT   GGTGATGAGT   GAGAAAAGCG   GTTTTGTCCT   GCCGGTGACG       180

TTGGAATGGG   AAGACATCCA   CTTCGTCCTG   CTCCTGTTGC   TGGTCGCCGC   TGTTGTCCTG       240
```

```
ACGATTCCGG CGATGCTGTC CTACCGTCAA TCTCCTGCTA CGGCGCTGCG TGGCGAGTAA    300
TAGGGTTGCG ACTCAGTCGC AAAACTAAGC TGTAGTGGCA TCGGACGTGT AGTTCTCTGC    360
GTCCGATGCT GTTTTTCCT  TACCTATTCA TCCCTTCCGA TTCTCATACT CACTCAACGG    420
CCTTCGTCCT TCGGTATTAT GGTTTGGGGC CAGTAACGAG CAGTAATACT GTTACTTATT    480
TCGCTAAATA ATATTTATAA TAATAGTAAC TCTATCAATT ATTATTGAAT TATTAGTATA    540
TAAAATGTTG ACTGATTGTA TATTAATTGA TAACTTTCGA CCTTGTTAAA TCCTAGTGAT    600
TATATTTGGT GTAACTAAAA ATAATTATAT TTACTCTCTG GTAAAGAGTT GATCTTTTAA    660
TCTTTGAGCA AAGTCGGTAA GAGAGGGTAA TATGGATCAT GAAATCCATT CCTTTATCAA    720
AAGGAAGTTG AAAGGAGTCG GTGATGTATG GTTTTCTTAT TTTATGATGA GTAAAAACTC    780
TACCAGCCAA CCTTATATTA TTTCGAATTA TCCAGAAGCA TGGATGAAGG AGTATATAAA    840
AAAAGAGATG TTTCTGAGTG ATCCTATCAT TGTTGCCTCA TTAGCTCGGA TCACGCCGTT    900
TTCTTGGGAT GATAATGATA TTGTGACGCT AAGAGCCAAG AATCAGGATG TCTTTATTTC    960
TTCCGTGCAG CACGATATAA GTTCAGGTTA TACCTTTGTT TTGCACGACC ATGATAATAA   1020
TGTGGCGACA CTGAGTATAG CGAATCACTT GGAAGATGCG AATTTCGAAA AATGTATGAA   1080
GAATCATGAA AATGATTTGC AGATGTTACT TGTGAATGTA CATGAAAAAG TGATGGCCTA   1140
TCAGCGAGCT ATCAACGATC AAGATAACCC CCCCGATAAT TCAAGAAACG CCTTACTCTC   1200
TCCGCGTGAA ACCGAAGTTC TTTTCCTGGT TAGTAGTGGA CGAACTTACA AAGAGGTTTC   1260
CCGTATATTA GGTATTAGTG AGGTCACCGT TAAGTTCCAC ATTAACAACT CAGTCCGTAA   1320
ATTGGATGTT ATCAATTCCC GCCATGCTAT AACTAAAGCA CTTGAGTTAA ATCTTTTCCA   1380
TTCCCCCTGT GAACCTGTAG TGATGAAGCA TATGGACGCC CGTTAGCGTG TATTAATGCT   1440
TGATAATAGG GAGGTACCTA TCCAAAAGAA TAGTAACTCC CTATCTAAAA GAAATACATT   1500
AGCTGAACTT TTACACGGTT AATATTTACC CTCGCCTTTT CTATGATATG TGACGAATTC   1560
AAACGTTGTT TTCTCTCATG TTGTTATTAA GGTAAGGGTT ATTACTGTGA GCAATAGTTT   1620
TTGCGTTGTT TATAAAGGTT CTGATACCGA TATAAATAAT ATCCAACGCG ACTTCGACGG   1680
AAAGGGCGAA CGATTATCTA ATGGCTATCT TTTTATCGAA CAGAATGGCC ATTATCAGAA   1740
GTGTGAGATG GAAAGAGGAA CGGCCTACCT GATAGGCTCG CTGTACAATC GGACGTTTCT   1800
GATCGGATTG GCCGGTGTGT GGGAAGGCGA GGCTTATCTG GCAAATGATG CCGAGCTGTT   1860
AGCGTTGCTG TTCACGCGTT TGGGAGCGAA TGCACTGGCG CTGGCTGAAG GTGCATTCTG   1920
CTTTTCTTAT GAGCCAAACG GCGAATTGAC GGTGATTACC GAGTCGCGTG GTTTCTCGCC   1980
GGTTCATGTC GTACAGGGCA AAAAGCCTG  GATGACCAAT AGCCTTAAAC TGGTTACTGC   2040
GGCAGAAGGT GAAGGCGCGC TGTGGTTTGA AGAAGAGGCG TTGGTGTGCC AGTCGCTGAT   2100
GCGAGCGGAT ACCTATACGC CGGTGAAAAA TGCGCAGCGT CTTAAGCCGG GAGCGGTGCA   2160
TGTTCTTACG CACGATAGCG AAGGTTATTC TTTCGTTGAA AGCCGCACGC TGACCACACC   2220
AGCCAGCAAC CAATTGTTAG CGCTCCCGCG TGAACCGCTG CTGGCATTGA TTGATCGCTA   2280
CCTTAATGCT CCGCTTGAGG ATTTAGCGCC GCGCTTTGAT ACCGTAGGAA TTCCCTTGTC   2340
AGGCGGTCTG GATTCCAGCC TGGTAACGGC GCTCGCCAGT CGTCATTTCA AAAAATTGAA   2400
TACGTATTCG ATTGGTACGG AACTCAGCAA TGAGTTTGAG TTTTCTCAAC AGGTTGCTGA   2460
TGCACTCGGT ACACATCATC AGATGAAAAT TCTGTCCGAA ACTGAAGTGA TCAACGGCAT   2520
CATCGAATCC ATCTATTACA ACGAAATATT TGACGGCTTA TCCGCTGAAA TCCAATCCGG   2580
GTTGTTCAAT GTCTATCGTC AGGCTCAGGG GCAGGTGTCT TGCATGCTCA CCGGATATGG   2640
```

```
TTCCGACCTG CTCTTTGGCG GCATACTGAA ACCAGGAGCG CAGTATGACA ATCCGAATCA    2700
GCTGCTTGCC GAGCAAGTGT ACCGGACGCG TTGGACAGGG GAGTTTGCTA CCCACGGTGC    2760
TTCCTGTTAC GGCATTGATA TTCGCCACCC CTTCTGGAGC CATTCCCTAA TCTCTCTATG    2820
TCATGCGCTA CATCCTGATT ACAAAATTTT CGACAACGAA GTCAAAAACA TCCTGCGTGA    2880
ATACGCCGAT TCGCTGCAAT TGCTGCCGAA AGACATTGTC TGGCGCAAGA AAATCGGCAT    2940
TCACGAAGGT TCCTCCGTCA ATCAGGCCTT TGCGAATGTT CTCGGGTCAA CGGTTGATAA    3000
CTACCAGACC AAAAGTCGCT TTACCTACCG TGTTTATCAA GCCTTCCTTC GTGGCCGTCT    3060
CTCCATTACA GATGTGACGC CCTCTCAGCT TAAAGATCTG ATTAAAAGG ATTAATTATG     3120
GTTTTTGAAG AGAATTCCGA TGAGGTCCGA GTGATCACGC TCGATCATCC GAACAAGCAT    3180
AACCCCTTTA GTCGAACGCT GGAAACCAGC GTGAAGGACG CGCTGGCGCG AGCCAACGCT    3240
GACGACAGCG TACGAGCTGT CGTGGTGTAT GGCGGGGCCG AGCGTTCCTT TTCCGCTGGC    3300
GGAGATTTCA ACGAAGTTAA GCAGCTATCG CGCAGCGAGG ACATCGAAGA GTGGATTGAC    3360
CGCGTGATTG ATTTGTATCA GGCCGTCCTG AATGTGAATA AACCGACGAT CGCAGCGGTG    3420
GATGGCTATG CGATTGGTAT GGGTTTCCAG TTCGCCCTGA TGTTTGACCA GAGACTGATG    3480
GCGTCGACAG CAAATTTTGT GATGCCGGAA CTTAAGCATG GTATCGGGTG CTCGGTTGGG    3540
GCGGCCATTC TGGGATTCAC CCACGGATTT AGCACAATGC AGGAAATCAT CTACCAGTGC    3600
CAGTCGCTCG ATGCTCCACG CTGTGTGGAC TACCGGCTGG TTAATCAGGT GGTGGAGAGC    3660
AGTGCGCTGC TGGATGCCGC TATCACACAG GCGCACGTGA TGGCTAGCTA CCCGGCTTCT    3720
GCATTCATCA ATACGAAACG AGCGGTTAAC AAACCGTTCA TCCATCTACT GGAACAAACC    3780
CGTGACGCTT CCAAAGCTGT CCATAAGGCA GCGTTCCAGG CTCGTGACGC TCAGGGACAT    3840
TTCAAAAATG TGCTTGGCAA AAAATACTGA GGATAAGGAA GAAAATGAGC GAAATAGTGA    3900
AGTTTAATCC GGTCATGGCA TCCGGTTTTG GCGCGTATAT CGATCATCGG GACTTTCTCG    3960
AAGCCAAGAC AGAAACGATT AAAAACTTAC TGATGCGTCA GGGATTTGTC GTGGTCAAAA    4020
ATCTCGATAT TGATAGTGAC ACATTCCGCG ATATCTACTC GGCTTACGGT ACGATCGTGG    4080
AGTATGCGGA TGAAAAGATC GGCGTAGGTT TCGGCTATCG CGATACGTTG AAGCTGGAAG    4140
GGGAAAAAGG AAAAATCGTT ACCGGACGTG GTCAACTTCC TTTCCACGCT GATGGCGGCC    4200
TGCTGCTGTC ACAGGTAGAT CAGGTTTTCC TCTACGCGGC CGAGATTAAA AACGTCAAAT    4260
TCCGTGGTGC AACAACGGTA TGCGACCATG CTCTGGCTTG TCAGGAAATG CCGGCTCACC    4320
TTCTGCGCGT ACTGGAAGAG GAAACGTTCG AAGTTCGTGT GCTAGAGCGG GGCTATTACG    4380
TGGATGTTTC ACCAGACGGT TGGTTCAAGG TGCCGGTCTT CACCGATCTG GATGGGTCA    4440
GAAAGATGCT GATTTATTTC CCATTTGACG AAGGACAACC GGCTAGCTGG GAGCCGCGGA    4500
TTGTCGGTTT CACCGATCAT GAAACCCAGG CATTCTTCCA GGAACTCGGG GCGTTTTAA    4560
AACAGCCACG CTACTACTAC AAACACTTCT GGGAAGATGG TGACCTGCTG ATTATGGACA    4620
ACCGTCGTGT CATTCATGAG CGTGAAGAGT TAACGATGA CGACATCGTA CGTCGTCTGT    4680
ATCGCGGACA AACCGCCGAT ATCTAACTCT CATGATTCCG GCGCGAAAAC GTGCCGGATT    4740
GATATGGATC TGGAACCATC ATGCCTAACG ATCTTTACGC TATCTACAAT CGTTACACGT    4800
CAAGGACCCT GTTTTTTAAA TACTGTGCGA CAGCGACGCT AACGCACAGA CTGACACGTC    4860
GGCTGTCGCT TTTTACGTTG AAAAGTGCC TTGCCCGTCC ACAGGGACGC CTTTTCTCTC     4920
TGGTTAATAG CATTTATTTT GGCGGAGAAA CGCTGGAAGA GGTTCAGAGT ACAGCAACTT    4980
TTCTGGCACG CTCTGGCATT GCTTGCGTAC TGGACTACGC CGTGGAAGGG GAAAATGACG    5040
```

```
AGACGCAGTT CGATAAGGCA ATGGAAAATA CGCTGCGCCT TATCGAGATG TCGCAGCAAA    5100
CGGATAGCCT GCCTTTTGTC GTGATTAAAC CGTCGTCTCT GGGTAGTGTT GCTGTGTATG    5160
CTCGGCAAAG TGAAAGGCTC GCGCTGGATG AAGCATCCGC CAGCGCATGG TCACGCATCG    5220
TTACGCGTTT CTCACGTCTG TTCGATTATG CCCGCTCTCA TGGCGTGCAT GTGATGGTTG    5280
ATGCAGAGCA GACCGCGATT CAGCCCGCAG TGGATCGTTT GGTTCTAGAC ATGATGCGTG    5340
AATTTAACCG CGATAGCGCG GTGATCACGC TGACGCTGCA ATTTTATCTA AAGGATCAAT    5400
TGCGTTTTCT CGACGAATGC TATCAGCGAG CCTGTCAGGA TAATTTCCTG TTCGGCGTGA    5460
AGTAGTGCG CGGTGCTTAT CTGGAAGAAG AGAAACGAGT GAACGGTGGC GTACGCTGTT    5520
TTGCAACCAA ACAGGAAACC GATCGTAGTT ATAACGCGGC GGTGGATTAC ATTGCACTGC    5580
GTCTGGATCG AATCGCACCG TTTTTCGCCA CGCACAACGA GGAAAGCCTC GCTTTGATTA    5640
TGTCGAGTGA GTCGCTACGC GCGGGGCGCA CCTGGGTAGG CCAGCTTTAC GGGTTGGGCG    5700
ATCATATTAC TTATTCGCTG CTGCAAACCG GTTTCCGCGT GTGCAAATAC CTGCCTTACG    5760
GTCCGCTCGA TAAGTCGTTG CCCTATTTAC TCCGCAGGAT TGAAGAGAAC GCGGTTGCCT    5820
CGGCAACCTT CAAAAAGGAA AATAAACTCT TGCAGAAGGA GTTGCTGCGC CGTCTCGTAG    5880
GAGGGATGTA ATGTCAAAAT TTCATTGTCA TATTCGCGAT ACGGCTATCG GTTTCCCCGT    5940
GTCGGAGGAT GAAAGCGTAC TCAGTTCAGC CTATGAAGCT GGTGTCGAAC TGCCTTATCG    6000
CTGTGCTTCT GGTTACTGTG GTGTATGCAA GGTGCGCCTG ACGTCCGGCA ACGTCAACAT    6060
GGATCATTCT GGTGGGATCT CACGTAAAGA TATCGCTGAT GGTTACATTC TACCTTGCTG    6120
TTCTGTGCCG CTCTCTAACC TCGAAATTGA ACCTGTATCG TCATGCTGAA GAAAACGCTA    6180
ATTGTTGGAC TGTGCTGTAC TTTCCCCCTC TTCTCCGCTC AAGCGGTGAA TACTGTTCCT    6240
GACGAGGTGG TTGTCAAAGG TGGCAATTTC TATGTTGGAT CGGTCTTCGG CTCGGAAGAC    6300
TATGCTGCTC ATGCCAACAC GTCTATCGCG TCTTTTGCCA TCACGAAAAC GGAAATTACC    6360
TATCGGCAGT ATCATGCGTT GCAAGAATGG GCGGACACAC ACGGTTATGA GCTTAGTGGC    6420
GGCTGCAATG GCGCGACTTT CGAAGATTGC TTACCGCCTG AACAGGATAA CAGTCTTCAT    6480
CCTGTCACGA ATGTATCTTG GTGGGATGCA GTGATTTTTG CCAATGTGCT CAGTGAACGG    6540
CAGCAGTTGC AGCCCTATTA CCTCACGATT GACGGTAAGA CGCTGAAACG CGTGCCGGAG    6600
GACGATAACG ATAAACTCAT ACGCGAGAAC CCGCAGGCTT TGGGGTATCG CTTGCCGACG    6660
CTGGCGGAAT GGCAAGTGGC AGCCAGAGGC GGAAAGAAGG GGCTGGCGCA GGGGACGTAC    6720
GGACAGCGCT ATGCCGGTAG CGAACAGCCG GACAGTGTGG CGCATTTTCC TTCTGACTCT    6780
CAATCATTCG GCACGGTGCC TGTGACCTCG AAGCGCCCCA ATGCTCTGGG GCTTACGAT    6840
ATGAGTGGCA ATGTATCCGA GTGGCTGAAT GAGTCTTATG CGGTGGAAGG CGGCAAAACC    6900
ATGTACTACT TTTGCGGCGG AAGTTATCTG GAACGCACGC ACAGTCTTGC TAGCTGCGAT    6960
CTGCATACGC CCGGTTTTTT CATGCCGGAT ATTGGTTTTC GACTAGTAAG GACACTTGAT    7020
GGTCAATAAG TTCGTAGGGT GGCTGGCGCT CTGTGCCATT AGCAACACGG CTGCTGCACT    7080
CTCTCCTGTG ACATTGAAAG ACGGCATCAA TCGGCTGGAT CTCAATCAGG GCGGCGGGAA    7140
CGATTATGTC GTTGTTGCCC AATTTGACAA CAATACCTCG CATCCTAATC TCGGGATGAC    7200
CTTTTTTGTC CGCCGTCCAG ACGGTGGGCA TAGCATTATG CCGGTAGCCA ACAGCAATAC    7260
GTTACCTGG TTCGACTATC GCCTGTCCGC TGCGGCGGAT TTTCTGGTGC AGGACAATCG    7320
GCTATTCCTG TCTGGAAAGC ATTACTTTCT GGTGACGGCA CGGAAGCAGG GTGAAAACGT    7380
CTTTGATCCC ACAAAAGTCG TTTTAACAAT TTACGACTTT AAAGCCTCAC GGGACGATCC    7440
```

-continued

```
CGGTGTACCA CTCTATGAAT GGTCGGAGCG CAAGCGTGTG GTAACACAAG ATACCTACCA    7500
ATCGGTCGAT GAGGCCTACA AGGAAGTGAA TGAGGCGATG CTGGCAAAAT GAAAATATCG    7560
GTATTAATCG CATCCGGGCT ATTGGCATCT TTCGGGGCGT GGGCGCAACT CAGTGAGCAG    7620
GATTACCAGC AACGCGTACA GGAGTTTTTT GATGCAGAAC CGCCGCTGTG TCTGGGCGAG    7680
AAGCAGTGGC CGGTTCATAG TCCCAAAGGT GATTCTCCCT GGAACAGTGG ACGGTTGCAT    7740
ACGCTTGTGG AAGCGGGGTT GGCATACGCG ACGCCTGAAG GAACAGGAAA GGTATATCGG    7800
TTATCGCCTG TAGGTGAGAA GAATTGGCGT CAACATGGCG ACCTTTGCTA TGGCCGTATG    7860
CAAGTGAGCC GTATTGAGAA AATCGATCGT GTGAACCAGG AACTGACGGT AGTGTATTTC    7920
ACTTATCATC TGACATCGTT GGAAAGTTGG GCTCATAACC GTTCGTTACG CTTTGCTTTT    7980
AGCGAGTTGG ATAATCTTGT CGGTGGAATG GAAACCACGC GTTATTCCGC TACGATTCGT    8040
GAGACGTTGG GCGGGGCGGC CAAATTGCAG GATTACCCCG TGCCGGTAGA GCTGGATTAC    8100
TAATCTGAAA TCTTATTGAC GTGACATAAA AAAAACAGGG TGAACGTGGT TCACCCTGCT    8160
GCATTTTACT GTCTTGGCGT GACGCCAGAG GGGATTAGCG TAAATCCAGC ATCGCGATAT    8220
GGTCCATATC GTCAAACGTT AGGTTTTCGC CGATCATGCC CCAGATAAAG GCATAGTTTT    8280
TGGTGCCGAC ACCGGTGTGA ATCGACCAAC TCGGGGAGAT CACGGCCTGC TCGTTATGCA    8340
T                                                                     8341
```

( 2 ) INFORMATION FOR SEQ ID NO: 2:

( i ) SEQUENCE CHARACTERISTICS:
        ( A ) LENGTH: 244 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Erwinia carotovora ( x i ) SEQUENCE DESCRIPTION: SEQ ID NO: 2:

```
Met Asp His Glu Ile His Ser Phe Ile Lys Arg Lys Leu Lys Gly Val
 1               5                  10                  15

Gly Asp Val Trp Phe Ser Tyr Phe Met Met Ser Lys Asn Ser Thr Ser
             20                  25                  30

Gln Pro Tyr Ile Ile Ser Asn Tyr Pro Glu Ala Trp Met Lys Glu Tyr
         35                  40                  45

Ile Lys Lys Glu Met Phe Leu Ser Asp Pro Ile Ile Val Ala Ser Leu
     50                  55                  60

Ala Arg Ile Thr Pro Phe Ser Trp Asp Asp Asn Asp Ile Val Thr Leu
 65                  70                  75                  80

Arg Ala Lys Asn Gln Asp Val Phe Ile Ser Ser Val Gln His Asp Ile
                 85                  90                  95

Ser Ser Gly Tyr Thr Phe Val Leu His Asp His Asp Asn Asn Val Ala
            100                 105                 110

Thr Leu Ser Ile Ala Asn His Leu Glu Asp Ala Asn Phe Glu Lys Cys
        115                 120                 125

Met Lys Asn His Glu Asn Asp Leu Gln Met Leu Leu Val Asn Val His
    130                 135                 140
```

-continued

| | | | | | | | | | | | | | | | |
|---|---|---|---|---|---|---|---|---|---|---|---|---|---|---|---|
| Glu | Lys | Val | Met | Ala | Tyr | Gln | Arg | Ala | Ile | Asn | Asp | Gln | Asp | Asn | Pro |
| 145 | | | | | 150 | | | | | 155 | | | | | 160 |
| Pro | Asp | Asn | Ser | Arg | Asn | Ala | Leu | Leu | Ser | Pro | Arg | Glu | Thr | Glu | Val |
| | | | | 165 | | | | | 170 | | | | | 175 | |
| Leu | Phe | Leu | Val | Ser | Ser | Gly | Arg | Thr | Tyr | Lys | Glu | Val | Ser | Arg | Ile |
| | | | 180 | | | | | 185 | | | | | 190 | | |
| Leu | Gly | Ile | Ser | Glu | Val | Thr | Val | Lys | Phe | His | Ile | Asn | Asn | Ser | Val |
| | | 195 | | | | | 200 | | | | | 205 | | | |
| Arg | Lys | Leu | Asp | Val | Ile | Asn | Ser | Arg | His | Ala | Ile | Thr | Lys | Ala | Leu |
| | 210 | | | | | 215 | | | | | 220 | | | | |
| Glu | Leu | Asn | Leu | Phe | His | Ser | Pro | Cys | Glu | Pro | Val | Val | Met | Lys | His |
| 225 | | | | | 230 | | | | | 235 | | | | | 240 |
| Met | Asp | Ala | Arg | | | | | | | | | | | | |

( 2 ) INFORMATION FOR SEQ ID NO: 3:

( i ) SEQUENCE CHARACTERISTICS:
        ( A ) LENGTH: 521 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Erwinia carotovora ( x i ) SEQUENCE DESCRIPTION: SEQ ID NO: 3:

| | | | | | | | | | | | | | | | |
|---|---|---|---|---|---|---|---|---|---|---|---|---|---|---|---|
| Val | Thr | Asn | Ser | Asn | Val | Val | Phe | Ser | His | Val | Val | Ile | Lys | Val | Arg |
| 1 | | | | 5 | | | | | 10 | | | | | 15 | |
| Val | Ile | Thr | Val | Ser | Asn | Ser | Phe | Cys | Val | Val | Tyr | Lys | Gly | Ser | Asp |
| | | | 20 | | | | | 25 | | | | | 30 | | |
| Thr | Asp | Ile | Asn | Asn | Ile | Gln | Arg | Asp | Phe | Asp | Gly | Lys | Gly | Glu | Arg |
| | | 35 | | | | | 40 | | | | | 45 | | | |
| Leu | Ser | Asn | Gly | Tyr | Leu | Phe | Ile | Glu | Gln | Asn | Gly | His | Tyr | Gln | Lys |
| | 50 | | | | | 55 | | | | | 60 | | | | |
| Cys | Glu | Met | Glu | Arg | Gly | Thr | Ala | Tyr | Leu | Ile | Gly | Ser | Leu | Tyr | Asn |
| 65 | | | | | 70 | | | | | 75 | | | | | 80 |
| Arg | Thr | Phe | Leu | Ile | Gly | Leu | Ala | Gly | Val | Trp | Glu | Gly | Glu | Ala | Tyr |
| | | | | 85 | | | | | 90 | | | | | 95 | |
| Leu | Ala | Asn | Asp | Ala | Glu | Leu | Leu | Ala | Leu | Leu | Phe | Thr | Arg | Leu | Gly |
| | | | | 100 | | | | | 105 | | | | | 110 | |
| Ala | Asn | Ala | Leu | Ala | Leu | Ala | Glu | Gly | Ala | Phe | Cys | Phe | Ser | Tyr | Glu |
| | | | 115 | | | | | 120 | | | | | 125 | | |
| Pro | Asn | Gly | Glu | Leu | Thr | Val | Ile | Thr | Glu | Ser | Arg | Gly | Phe | Ser | Pro |
| | | | 130 | | | | | 135 | | | | | 140 | | |
| Val | His | Val | Val | Gln | Gly | Lys | Lys | Ala | Trp | Met | Thr | Asn | Ser | Leu | Lys |
| 145 | | | | | 150 | | | | | 155 | | | | | 160 |
| Leu | Val | Thr | Ala | Ala | Glu | Gly | Glu | Gly | Ala | Leu | Trp | Phe | Glu | Glu | Glu |
| | | | | 165 | | | | | 170 | | | | | 175 | |
| Ala | Leu | Val | Cys | Gln | Ser | Leu | Met | Arg | Ala | Asp | Thr | Tyr | Thr | Pro | Val |
| | | | 180 | | | | | 185 | | | | | 190 | | |
| Lys | Asn | Ala | Gln | Arg | Leu | Lys | Pro | Gly | Ala | Val | His | Val | Leu | Thr | His |
| | | | 195 | | | | | 200 | | | | | 205 | | |
| Asp | Ser | Glu | Gly | Tyr | Ser | Phe | Val | Glu | Ser | Arg | Thr | Leu | Thr | Thr | Pro |
| | | | 210 | | | | | 215 | | | | | 220 | | |

```
Ala Ser Asn Gln Leu Leu Ala Leu Pro Arg Glu Pro Leu Leu Ala Leu
225                 230                 235                 240

Ile Asp Arg Tyr Leu Asn Ala Pro Leu Glu Asp Leu Ala Pro Arg Phe
                245                 250                 255

Asp Thr Val Gly Ile Pro Leu Ser Gly Gly Leu Asp Ser Ser Leu Val
            260                 265                 270

Thr Ala Leu Ala Ser Arg His Phe Lys Lys Leu Asn Thr Tyr Ser Ile
        275                 280                 285

Gly Thr Glu Leu Ser Asn Glu Phe Glu Phe Ser Gln Gln Val Ala Asp
    290                 295                 300

Ala Leu Gly Thr His His Gln Met Lys Ile Leu Ser Glu Thr Glu Val
305                 310                 315                 320

Ile Asn Gly Ile Ile Glu Ser Ile Tyr Tyr Asn Glu Ile Phe Asp Gly
                325                 330                 335

Leu Ser Ala Glu Ile Gln Ser Gly Leu Phe Asn Val Tyr Arg Gln Ala
            340                 345                 350

Gln Gly Gln Val Ser Cys Met Leu Thr Gly Tyr Gly Ser Asp Leu Leu
        355                 360                 365

Phe Gly Gly Ile Leu Lys Pro Gly Ala Gln Tyr Asp Asn Pro Asn Gln
    370                 375                 380

Leu Leu Ala Glu Gln Val Tyr Arg Thr Arg Trp Thr Gly Glu Phe Ala
385                 390                 395                 400

Thr His Gly Ala Ser Cys Tyr Gly Ile Asp Ile Arg His Pro Phe Trp
            405                 410                 415

Ser His Ser Leu Ile Ser Leu Cys His Ala Leu His Pro Asp Tyr Lys
        420                 425                 430

Ile Phe Asp Asn Glu Val Lys Asn Ile Leu Arg Glu Tyr Ala Asp Ser
    435                 440                 445

Leu Gln Leu Leu Pro Lys Asp Ile Val Trp Arg Lys Lys Ile Gly Ile
    450                 455                 460

His Glu Gly Ser Ser Val Asn Gln Ala Phe Ala Asn Val Leu Gly Ser
465                 470                 475                 480

Thr Val Asp Asn Tyr Gln Thr Lys Ser Arg Phe Thr Tyr Arg Val Tyr
            485                 490                 495

Gln Ala Phe Leu Arg Gly Arg Leu Ser Ile Thr Asp Val Thr Pro Ser
        500                 505                 510

Gln Leu Lys Asp Leu Ile Lys Lys Asp
        515                 520
```

(2) INFORMATION FOR SEQ ID NO: 4:

(i) SEQUENCE CHARACTERISTICS:
        (A) LENGTH: 250 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Erwinia carotovora (xi) SEQUENCE DESCRIPTION: SEQ ID NO: 4:

```
Met Val Phe Glu Glu Asn Ser Asp Glu Val Arg Val Ile Thr Leu Asp
1               5                   10                  15

His Pro Asn Lys His Asn Pro Phe Ser Arg Thr Leu Glu Thr Ser Val
            20                  25                  30
```

```
         Lys   Asp   Ala   Leu   Ala   Arg   Ala   Asn   Ala   Asp   Asp   Ser   Val   Arg   Ala   Val
                     3 5                           4 0                          4 5

Val   Val   Tyr   Gly   Gly   Ala   Glu   Arg   Ser   Phe   Ser   Ala   Gly   Gly   Asp   Phe
               5 0                          5 5                          6 0

Asn   Glu   Val   Lys   Gln   Leu   Ser   Arg   Ser   Glu   Asp   Ile   Glu   Glu   Trp   Ile
         6 5                           7 0                          7 5                               8 0

Asp   Arg   Val   Ile   Asp   Leu   Tyr   Gln   Ala   Val   Leu   Asn   Val   Asn   Lys   Pro
                                 8 5                           9 0                          9 5

Thr   Ile   Ala   Ala   Val   Asp   Gly   Tyr   Ala   Ile   Gly   Met   Gly   Phe   Gln   Phe
                           1 0 0                         1 0 5                         1 1 0

Ala   Leu   Met   Phe   Asp   Gln   Arg   Leu   Met   Ala   Ser   Thr   Ala   Asn   Phe   Val
                     1 1 5                         1 2 0                         1 2 5

Met   Pro   Glu   Leu   Lys   His   Gly   Ile   Gly   Cys   Ser   Val   Gly   Ala   Ala   Ile
               1 3 0                         1 3 5                         1 4 0

Leu   Gly   Phe   Thr   His   Gly   Phe   Ser   Thr   Met   Gln   Glu   Ile   Ile   Tyr   Gln
         1 4 5                         1 5 0                         1 5 5                         1 6 0

Cys   Gln   Ser   Leu   Asp   Ala   Pro   Arg   Cys   Val   Asp   Tyr   Arg   Leu   Val   Asn
                                 1 6 5                         1 7 0                         1 7 5

Gln   Val   Val   Glu   Ser   Ser   Ala   Leu   Leu   Asp   Ala   Ala   Ile   Thr   Gln   Ala
                           1 8 0                         1 8 5                         1 9 0

His   Val   Met   Ala   Ser   Tyr   Pro   Ala   Ser   Ala   Phe   Ile   Asn   Thr   Lys   Arg
                     1 9 5                         2 0 0                         2 0 5

Ala   Val   Asn   Lys   Pro   Phe   Ile   His   Leu   Leu   Glu   Gln   Thr   Arg   Asp   Ala
               2 1 0                         2 1 5                         2 2 0

Ser   Lys   Ala   Val   His   Lys   Ala   Ala   Phe   Gln   Ala   Arg   Asp   Ala   Gln   Gly
         2 2 5                         2 3 0                         2 3 5                         2 4 0

His   Phe   Lys   Asn   Val   Leu   Gly   Lys   Lys   Tyr
                                 2 4 5                         2 5 0
```

( 2 ) INFORMATION FOR SEQ ID NO: 5:

( i ) SEQUENCE CHARACTERISTICS:
        ( A ) LENGTH: 273 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Erwinia carotovora ( x i ) SEQUENCE DESCRIPTION: SEQ ID NO: 5:

```
         Met   Ser   Glu   Ile   Val   Lys   Phe   Asn   Pro   Val   Met   Ala   Ser   Gly   Phe   Gly
         1                       5                           1 0                          1 5

Ala   Tyr   Ile   Asp   His   Arg   Asp   Phe   Leu   Glu   Ala   Lys   Thr   Glu   Thr   Ile
                           2 0                          2 5                          3 0

Lys   Asn   Leu   Leu   Met   Arg   Gln   Gly   Phe   Val   Val   Val   Lys   Asn   Leu   Asp
                     3 5                          4 0                          4 5

Ile   Asp   Ser   Asp   Thr   Phe   Arg   Asp   Ile   Tyr   Ser   Ala   Tyr   Gly   Thr   Ile
                     5 0                          5 5                          6 0

Val   Glu   Tyr   Ala   Asp   Glu   Lys   Ile   Gly   Val   Gly   Phe   Gly   Tyr   Arg   Asp
         6 5                          7 0                          7 5                               8 0

Thr   Leu   Lys   Leu   Glu   Gly   Glu   Lys   Gly   Lys   Ile   Val   Thr   Gly   Arg   Gly
                                 8 5                          9 0                          9 5

Gln   Leu   Pro   Phe   His   Ala   Asp   Gly   Gly   Leu   Leu   Leu   Ser   Gln   Val   Asp
```

-continued

|     |     |     |     | 100 |     |     |     |     | 105 |     |     |     |     | 110 |     |
|-----|-----|-----|-----|-----|-----|-----|-----|-----|-----|-----|-----|-----|-----|-----|-----|

Gln Val Phe Leu Tyr Ala Ala Glu Ile Lys Asn Val Lys Phe Arg Gly
            115                 120                 125

Ala Thr Thr Val Cys Asp His Ala Leu Ala Cys Gln Glu Met Pro Ala
        130                 135                 140

His Leu Leu Arg Val Leu Glu Glu Thr Phe Glu Val Arg Val Leu
145                     150                 155                 160

Glu Arg Gly Tyr Tyr Val Asp Val Ser Pro Asp Gly Trp Phe Lys Val
                    165                 170                 175

Pro Val Phe Thr Asp Leu Gly Trp Val Arg Lys Met Leu Ile Tyr Phe
            180                 185                 190

Pro Phe Asp Glu Gly Gln Pro Ala Ser Trp Glu Pro Arg Ile Val Gly
        195                 200                 205

Phe Thr Asp His Glu Thr Gln Ala Phe Phe Gln Glu Leu Gly Ala Phe
            210                 215                 220

Leu Lys Gln Pro Arg Tyr Tyr Lys His Phe Trp Glu Asp Gly Asp
225                 230                 235                 240

Leu Leu Ile Met Asp Asn Arg Arg Val Ile His Glu Arg Glu Glu Phe
                245                 250                 255

Asn Asp Asp Asp Ile Val Arg Arg Leu Tyr Arg Gly Gln Thr Ala Asp
            260                 265                 270

Ile ( 2 ) INFORMATION FOR SEQ ID NO: 6:

( i ) SEQUENCE CHARACTERISTICS:
        ( A ) LENGTH: 376 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Erwinia carotovora ( x i ) SEQUENCE DESCRIPTION: SEQ ID NO: 6:

Met Pro Asn Asp Leu Tyr Ala Ile Tyr Asn Arg Tyr Thr Ser Arg Thr
1               5                   10                  15

Leu Phe Phe Lys Tyr Cys Ala Thr Ala Thr Leu Thr His Arg Leu Thr
            20                  25                  30

Arg Arg Leu Ser Leu Phe Thr Leu Lys Lys Cys Leu Ala Arg Pro Gln
        35                  40                  45

Gly Arg Leu Phe Ser Leu Val Asn Ser Ile Tyr Phe Gly Gly Glu Thr
    50                  55                  60

Leu Glu Glu Val Gln Ser Thr Ala Thr Phe Leu Ala Arg Ser Gly Ile
65                  70                  75                  80

Ala Cys Val Leu Asp Tyr Ala Val Glu Gly Glu Asn Asp Glu Thr Gln
                85                  90                  95

Phe Asp Lys Ala Met Glu Asn Thr Leu Arg Leu Ile Glu Met Ser Gln
            100                 105                 110

Gln Thr Asp Ser Leu Pro Phe Val Val Ile Lys Pro Ser Ser Leu Gly
        115                 120                 125

Ser Val Ala Val Tyr Ala Arg Gln Ser Glu Arg Leu Ala Leu Asp Glu
    130                 135                 140

Ala Ser Ala Ser Ala Trp Ser Arg Ile Val Thr Arg Phe Ser Arg Leu

-continued

| | | | | 145 | | | | | 150 | | | | | 155 | | | | | 160 |
|---|---|---|---|---|---|---|---|---|---|---|---|---|---|---|---|---|---|---|---|
| Phe | Asp | Tyr | Ala | Arg<br>165 | Ser | His | Gly | Val | His<br>170 | Val | Met | Val | Asp | Ala<br>175 | Glu |
| Gln | Thr | Ala | Ile<br>180 | Gln | Pro | Ala | Val | Asp<br>185 | Arg | Leu | Val | Leu<br>190 | Asp | Met | Met |
| Arg | Glu | Phe<br>195 | Asn | Arg | Asp | Ser | Ala<br>200 | Val | Ile | Thr | Leu<br>205 | Thr | Leu | Gln | Phe |
| Tyr | Leu<br>210 | Lys | Asp | Gln | Leu | Arg<br>215 | Phe | Leu | Asp | Glu | Cys<br>220 | Tyr | Gln | Arg | Ala |
| Cys<br>225 | Gln | Asp | Asn | Phe | Leu<br>230 | Phe | Gly | Val | Lys | Val<br>235 | Val | Arg | Gly | Ala | Tyr<br>240 |
| Leu | Glu | Glu | Glu | Lys<br>245 | Arg | Val | Asn | Gly | Val<br>250 | Arg | Cys | Phe | Ala<br>255 | Thr |
| Lys | Gln | Glu | Thr<br>260 | Asp | Arg | Ser | Tyr | Asn<br>265 | Ala | Ala | Val | Asp | Tyr<br>270 | Ile | Ala |
| Leu | Arg | Leu<br>275 | Asp | Arg | Ile | Ala | Pro<br>280 | Phe | Phe | Ala | Thr | His<br>285 | Asn | Glu | Glu |
| Ser | Leu<br>290 | Ala | Leu | Ile | Met | Ser<br>295 | Ser | Glu | Ser | Leu | Arg<br>300 | Ala | Gly | Arg | Thr |
| Trp<br>305 | Val | Gly | Gln | Leu | Tyr<br>310 | Gly | Leu | Gly | Asp | His<br>315 | Ile | Thr | Tyr | Ser | Leu<br>320 |
| Leu | Gln | Thr | Gly | Phe<br>325 | Arg | Val | Cys | Lys | Tyr<br>330 | Leu | Pro | Tyr | Gly | Pro<br>335 | Leu |
| Asp | Lys | Ser | Leu<br>340 | Pro | Tyr | Leu | Leu | Arg<br>345 | Arg | Ile | Glu | Glu | Asn<br>350 | Ala | Val |
| Ala | Ser | Ala<br>355 | Thr | Phe | Lys | Lys | Glu<br>360 | Asn | Lys | Leu | Leu | Gln<br>365 | Lys | Glu | Leu |
| Leu | Arg<br>370 | Arg | Leu | Val | Gly | Gly<br>375 | Met | | | | | | | | |

( 2 ) INFORMATION FOR SEQ ID NO: 7:

( i ) SEQUENCE CHARACTERISTICS:
        ( A ) LENGTH: 92 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Erwinia carotovora ( x i ) SEQUENCE DESCRIPTION: SEQ ID NO: 7:

| Met<br>1 | Ser | Lys | Phe | His<br>5 | Cys | His | Ile | Arg | Asp<br>10 | Thr | Ala | Ile | Gly | Phe<br>15 | Pro |
|---|---|---|---|---|---|---|---|---|---|---|---|---|---|---|---|
| Val | Ser | Glu | Asp<br>20 | Glu | Ser | Val | Leu | Ser<br>25 | Ser | Ala | Tyr | Glu | Ala<br>30 | Gly | Val |
| Glu | Leu | Pro<br>35 | Tyr | Arg | Cys | Ala | Ser<br>40 | Gly | Tyr | Cys | Gly | Val<br>45 | Cys | Lys | Val |
| Arg | Leu<br>50 | Thr | Ser | Gly | Asn | Val<br>55 | Asn | Met | Asp | His | Ser<br>60 | Gly | Gly | Ile | Ser |
| Arg<br>65 | Lys | Asp | Ile | Ala | Asp<br>70 | Gly | Tyr | Ile | Leu | Pro<br>75 | Cys | Cys | Ser | Val | Pro<br>80 |
| Leu | Ser | Asn | Leu | Glu<br>85 | Ile | Glu | Pro | Val | Ser<br>90 | Ser | Cys | | | | |

(2) INFORMATION FOR SEQ ID NO: 8:

(i) SEQUENCE CHARACTERISTICS:
        (A) LENGTH: 288 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Erwinia carotovora (xi) SEQUENCE DESCRIPTION: SEQ ID NO: 8:

```
Met Leu Lys Lys Thr Leu Ile Val Gly Leu Cys Cys Thr Phe Pro Leu
  1               5                  10                  15

Phe Ser Ala Gln Ala Val Asn Thr Val Pro Asp Glu Val Val Lys
             20                  25                  30

Gly Gly Asn Phe Tyr Val Gly Ser Val Phe Gly Ser Glu Asp Tyr Ala
             35                  40                  45

Ala His Ala Asn Thr Ser Ile Ala Ser Phe Ala Ile Thr Lys Thr Glu
     50                  55                  60

Ile Thr Tyr Arg Gln Tyr His Ala Leu Gln Glu Trp Ala Asp Thr His
 65                  70                  75                  80

Gly Tyr Glu Leu Ser Gly Gly Cys Asn Gly Ala Thr Phe Glu Asp Cys
                 85                  90                  95

Leu Pro Pro Glu Gln Asp Asn Ser Leu His Pro Val Thr Asn Val Ser
             100                 105                 110

Trp Trp Asp Ala Val Ile Phe Ala Asn Val Leu Ser Glu Arg Gln Gln
             115                 120                 125

Leu Gln Pro Tyr Tyr Leu Thr Ile Asp Gly Lys Thr Leu Lys Arg Val
         130                 135                 140

Pro Glu Asp Asp Asn Asp Lys Leu Ile Arg Glu Asn Pro Gln Ala Leu
145                 150                 155                 160

Gly Tyr Arg Leu Pro Thr Leu Ala Glu Trp Gln Val Ala Ala Arg Gly
                 165                 170                 175

Gly Lys Lys Gly Leu Ala Gln Gly Thr Tyr Gly Gln Arg Tyr Ala Gly
             180                 185                 190

Ser Glu Gln Pro Asp Ser Val Ala His Phe Pro Ser Asp Ser Gln Ser
         195                 200                 205

Phe Gly Thr Val Pro Val Thr Ser Lys Arg Pro Asn Ala Leu Gly Leu
     210                 215                 220

Tyr Asp Met Ser Gly Asn Val Ser Glu Trp Leu Asn Glu Ser Tyr Ala
225                 230                 235                 240

Val Glu Gly Gly Lys Thr Met Tyr Tyr Phe Cys Gly Gly Ser Tyr Leu
             245                 250                 255

Glu Arg Thr His Ser Leu Ala Ser Cys Asp Leu His Thr Pro Gly Phe
         260                 265                 270

Phe Met Pro Asp Ile Gly Phe Arg Leu Val Arg Thr Leu Asp Gly Gln
     275                 280                 285
```

(2) INFORMATION FOR SEQ ID NO: 9:

(i) SEQUENCE CHARACTERISTICS:
        (A) LENGTH: 177 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
    (A) ORGANISM: Erwinia carotovora (xi) SEQUENCE DESCRIPTION: SEQ ID NO: 9:

| Met | Val | Asn | Lys | Phe | Val | Gly | Trp | Leu | Ala | Leu | Cys | Ala | Ile | Ser | Asn |
|---|---|---|---|---|---|---|---|---|---|---|---|---|---|---|---|
| 1 | | | | 5 | | | | | 10 | | | | | 15 | |

| Thr | Ala | Ala | Ala | Leu | Ser | Pro | Val | Thr | Leu | Lys | Asp | Gly | Ile | Asn | Arg |
|---|---|---|---|---|---|---|---|---|---|---|---|---|---|---|---|
| | | | 20 | | | | 25 | | | | | 30 | | | |

| Leu | Asp | Leu | Asn | Gln | Gly | Gly | Gly | Asn | Asp | Tyr | Val | Val | Val | Ala | Gln |
|---|---|---|---|---|---|---|---|---|---|---|---|---|---|---|---|
| | | 35 | | | | 40 | | | | | 45 | | | | |

| Phe | Asp | Asn | Asn | Thr | Ser | His | Pro | Asn | Leu | Gly | Met | Thr | Phe | Phe | Val |
|---|---|---|---|---|---|---|---|---|---|---|---|---|---|---|---|
| | 50 | | | | | 55 | | | | | 60 | | | | |

| Arg | Arg | Pro | Asp | Gly | Gly | His | Ser | Ile | Met | Pro | Val | Ala | Asn | Ser | Asn |
|---|---|---|---|---|---|---|---|---|---|---|---|---|---|---|---|
| 65 | | | | | 70 | | | | | 75 | | | | | 80 |

| Thr | Phe | Thr | Trp | Phe | Asp | Tyr | Arg | Leu | Ser | Ala | Ala | Ala | Asp | Phe | Leu |
|---|---|---|---|---|---|---|---|---|---|---|---|---|---|---|---|
| | | | | 85 | | | | | 90 | | | | | 95 | |

| Val | Gln | Asp | Asn | Arg | Leu | Phe | Leu | Ser | Gly | Lys | His | Tyr | Phe | Leu | Val |
|---|---|---|---|---|---|---|---|---|---|---|---|---|---|---|---|
| | | | 100 | | | | | 105 | | | | | 110 | | |

| Thr | Ala | Arg | Lys | Gln | Gly | Glu | Asn | Val | Phe | Asp | Pro | Thr | Lys | Val | Val |
|---|---|---|---|---|---|---|---|---|---|---|---|---|---|---|---|
| | | | 115 | | | | 120 | | | | | 125 | | | |

| Leu | Thr | Ile | Tyr | Asp | Phe | Lys | Ala | Ser | Arg | Asp | Asp | Pro | Gly | Val | Pro |
|---|---|---|---|---|---|---|---|---|---|---|---|---|---|---|---|
| | | 130 | | | | | 135 | | | | | 140 | | | |

| Leu | Tyr | Glu | Trp | Ser | Glu | Arg | Lys | Arg | Val | Val | Thr | Gln | Asp | Thr | Tyr |
|---|---|---|---|---|---|---|---|---|---|---|---|---|---|---|---|
| 145 | | | | | 150 | | | | | 155 | | | | | 160 |

| Gln | Ser | Val | Asp | Glu | Ala | Tyr | Lys | Glu | Val | Asn | Glu | Ala | Met | Leu | Ala |
|---|---|---|---|---|---|---|---|---|---|---|---|---|---|---|---|
| | | | | 165 | | | | | 170 | | | | | 175 | |

Lys (2) INFORMATION FOR SEQ ID NO: 10:

(i) SEQUENCE CHARACTERISTICS:
    (A) LENGTH: 184 amino acids
    (B) TYPE: amino acid
    (C) STRANDEDNESS:
    (D) TOPOLOGY: linear (ii) MOLECULE TYPE: protein (iii) HYPOTHETICAL: NO (vi) ORIGINAL SOURCE:
    (A) ORGANISM: Erwinia carotovora (xi) SEQUENCE DESCRIPTION: SEQ ID NO: 10:

| Met | Lys | Ile | Ser | Val | Leu | Ile | Ala | Ser | Gly | Leu | Leu | Ala | Ser | Phe | Gly |
|---|---|---|---|---|---|---|---|---|---|---|---|---|---|---|---|
| 1 | | | | 5 | | | | | 10 | | | | | 15 | |

| Ala | Trp | Ala | Gln | Leu | Ser | Glu | Gln | Asp | Tyr | Gln | Gln | Arg | Val | Gln | Glu |
|---|---|---|---|---|---|---|---|---|---|---|---|---|---|---|---|
| | | | 20 | | | | 25 | | | | | 30 | | | |

| Phe | Phe | Asp | Ala | Glu | Pro | Pro | Leu | Cys | Leu | Gly | Glu | Lys | Gln | Trp | Pro |
|---|---|---|---|---|---|---|---|---|---|---|---|---|---|---|---|
| | | | 35 | | | | 40 | | | | | 45 | | | |

| Val | His | Ser | Pro | Lys | Gly | Asp | Ser | Pro | Trp | Asn | Ser | Gly | Arg | Leu | His |
|---|---|---|---|---|---|---|---|---|---|---|---|---|---|---|---|
| | | 50 | | | | | 55 | | | | | 60 | | | |

| Thr | Leu | Val | Glu | Ala | Gly | Leu | Ala | Tyr | Ala | Thr | Pro | Glu | Gly | Thr | Gly |
|---|---|---|---|---|---|---|---|---|---|---|---|---|---|---|---|
| 65 | | | | | 70 | | | | | 75 | | | | | 80 |

| Lys | Val | Tyr | Arg | Leu | Ser | Pro | Val | Gly | Glu | Lys | Asn | Trp | Arg | Gln | His |
|---|---|---|---|---|---|---|---|---|---|---|---|---|---|---|---|
| | | | | 85 | | | | | 90 | | | | | 95 | |

| | | | | | | | | | | | | | | |
|---|---|---|---|---|---|---|---|---|---|---|---|---|---|---|
|Gly|Asp|Leu|Cys<br>100|Tyr|Gly|Arg|Met|Gln<br>105|Val|Ser|Arg|Ile|Glu<br>110|Lys|Ile|
|Asp|Arg|Val<br>115|Asn|Gln|Glu|Leu|Thr<br>120|Val|Val|Tyr|Phe|Thr<br>125|Tyr|His|Leu|
|Thr|Ser<br>130|Leu|Glu|Ser|Trp|Ala<br>135|His|Asn|Arg|Ser|Leu<br>140|Arg|Phe|Ala|Phe|
|Ser<br>145|Glu|Leu|Asp|Asn|Leu<br>150|Val|Gly|Gly|Met|Glu<br>155|Thr|Thr|Arg|Tyr|Ser<br>160|
|Ala|Thr|Ile|Arg|Glu<br>165|Thr|Leu|Gly|Gly|Ala<br>170|Ala|Lys|Leu|Gln|Asp<br>175|Tyr|
|Pro|Val|Pro|Val<br>180|Glu|Leu|Asp|Tyr| | | | | | | | |

( 2 ) INFORMATION FOR SEQ ID NO: 11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE PRIMER"

( i i i ) HYPOTHETICAL: NO ( i v ) ANTI-SENSE: NO ( x i ) SEQUENCE DESCRIPTION: SEQ ID NO: 11:

CCGSGACATC TACTCSGC                                  18

( 2 ) INFORMATION FOR SEQ ID NO: 12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE PRIMER"

( i i i ) HYPOTHETICAL: NO ( i v ) ANTI-SENSE: NO ( x i ) SEQUENCE DESCRIPTION: SEQ ID NO: 12:

CCGTCCTCCC AGAAGTGC                                  18